United States Patent
Thewes et al.

(10) Patent No.: US 7,223,330 B2
(45) Date of Patent: May 29, 2007

(54) BIOSENSOR, BIOSENSOR ARRAY AND METHOD FOR DETECTING MACROMOLECULAR BIOPOLYMERS WITH A BIOSENSOR

(75) Inventors: Roland Thewes, Grobenzell (DE); Werner Weber, Munich (DE)

(73) Assignee: Siemens Aktiengesellschaft (DE)

( * ) Notice: Subject to any disclaimer, the term of this patent is extended or adjusted under 35 U.S.C. 154(b) by 511 days.

(21) Appl. No.: 10/239,481

(22) PCT Filed: Mar. 29, 2001

(86) PCT No.: PCT/DE01/01240

§ 371 (c)(1),
(2), (4) Date: Jan. 16, 2003

(87) PCT Pub. No.: WO01/75149

PCT Pub. Date: Oct. 11, 2001

(65) Prior Publication Data

US 2004/0045839 A1 Mar. 11, 2004

(30) Foreign Application Priority Data

Mar. 30, 2000 (DE) .................... 100 15 959

(51) Int. Cl.
*G01N 27/26* (2006.01)
(52) U.S. Cl. .............. 205/777.5; 435/7.1; 435/7.9; 435/7.91
(58) Field of Classification Search .......... 205/777.5; 435/7.1, 7.9, 7.91, 177
See application file for complete search history.

(56) References Cited

U.S. PATENT DOCUMENTS

| | | | |
|---|---|---|---|
| 6,294,062 B1 * | 9/2001 | Buck et al. | 204/400 |
| 6,440,662 B1 * | 8/2002 | Gerwen et al. | 435/6 |
| 6,682,648 B1 * | 1/2004 | MacPhee et al. | 205/777.5 |

FOREIGN PATENT DOCUMENTS

| | | |
|---|---|---|
| JP | 08128987 | 5/1996 |
| JP | 2000505890 | 5/2000 |
| WO | WO 97/27474 | 7/1997 |
| WO | WO 99/07879 | 2/1999 |
| WO | WO 99/60399 | 11/1999 |
| WO | WO 99/63346 | 12/1999 |

OTHER PUBLICATIONS

R. Hintsche et al., Microbiosensors Using Electrodes Made in Si-Technology, Frontiers in Biosensorics, Fundamental Aspects, edited by F.W. Scheller et al., Dirk Hauser Verlag, Basel, pp. 267-283, 1997.

(Continued)

*Primary Examiner*—Nam Nguyen
*Assistant Examiner*—Anthony Fick
(74) *Attorney, Agent, or Firm*—Jeffrey R. Stone; Altera Law Group, LLC

(57) ABSTRACT

The inventive biosensor has three electrodes, the first electrode having a retaining area for retaining probe molecules which bind with the macromolecular biopolymers. The second electrode and the third electrode are configured in such a way that the redox process is part of a redox recycling system on said second and third electrodes.

14 Claims, 16 Drawing Sheets

OTHER PUBLICATIONS

N.L. Thompson, B.C. Lagerholm, Total Internal Reflection Fluorescence: Applications in Cellular Biophysics, Current Opinion in Biotechnology, vol. 8, pp. 58-64, 1997.

P. Cuatrecasas, Affinity Chromatography of Macromolecules, Advances in Enzymology, vol. 36, pp. 29-89, 1972.

P. Van Gerwen, Nanoscaled Interdigitated Electrode Arrays for Biochemical Sensors, IEEE, Intern. Conf. on Solid-State Sensors and Actuators, Chicago, pp. 907-910, Jun. 16-19, 1997.

M. Paeschke et al., Voltametric Multichannel Measurements Using Silicon Fabricated Microelectrode Arrays, Electronalysis, vol. 7, No. 1, pp. 1-8, 1996.

Niwa O et al: "Small-volume voltammetric detection of 4-aminophenol with interdigitated array electrodes and its application to electrochemical enzyme immunoassay", vol. 65, 11, 1993 pp. 1559-1563.

* cited by examiner

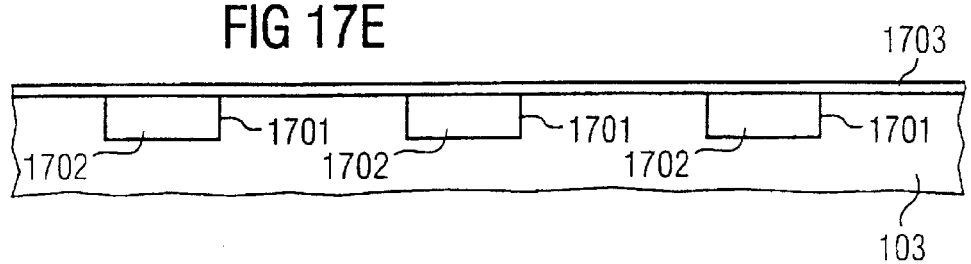
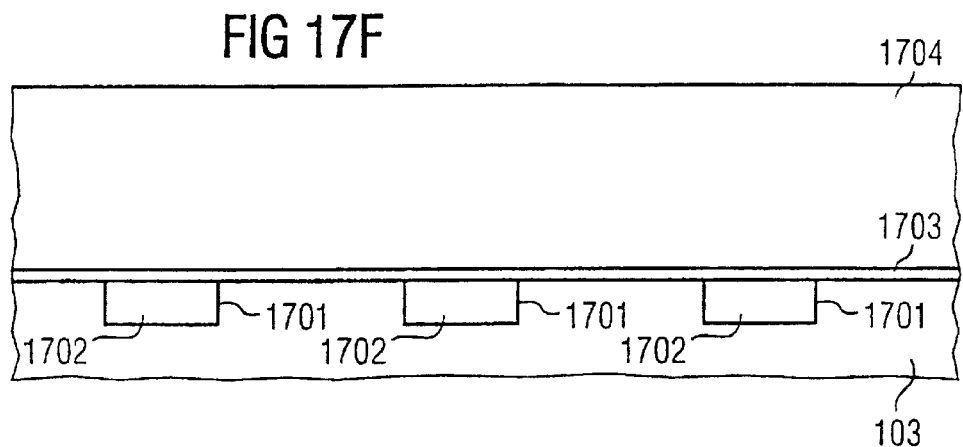
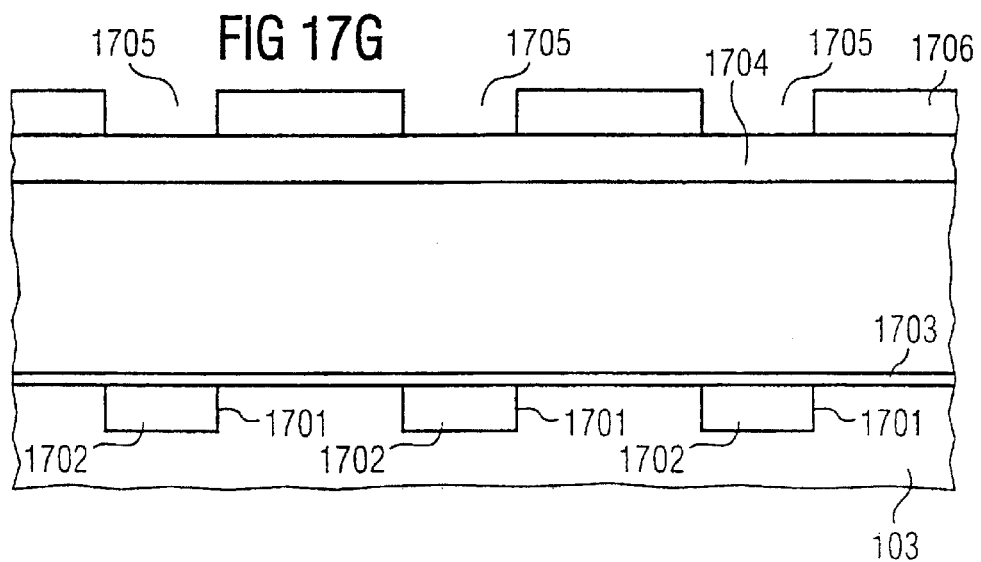

BIOSENSOR, BIOSENSOR ARRAY AND METHOD FOR DETECTING MACROMOLECULAR BIOPOLYMERS WITH A BIOSENSOR

The invention relates to a biosensor, a biosensor array and a method for detecting macromolecular biopolymers using a biosensor.

A biosensor of this type, a biosensor array of this type and a method of this type are known from [1] and [4].

FIG. 2a and FIG. 2b show such a sensor, as described in [1] and [4]. The sensor 200 has two electrodes 201, 202 made of gold, which are embedded in an insulator layer 203 made of insulator material. Electrode terminals 204, 205, to which the electrical potential applied to the electrodes 201, 202 can be delivered, are connected to the electrodes 201, 202. The electrodes 201, 202 are arranged as planar electrodes. DNA probe molecules 206 are immobilized on each electrode 201, 202 (cf. FIG. 2a). The immobilization is carried out according to the so-called gold-sulfur coupling. The analyte to be analyzed, for example an electrolyte 207, is applied to the electrodes 201, 202.

If DNA strands 208 with a sequence which is complementary to the sequence of the DNA probe molecules 206 are contained in the electrolyte 207, then these DNA strands 208 hybridize with the DNA probe molecules 206 (cf. FIG. 2b).

Hybridization of a DNA probe molecule 206 and a DNA strand 208 takes place only if the sequences of the respective DNA probe molecule 206 and of the corresponding DNA strand 208 are complementary to one another. If this is not the case, then no hybridization takes place. A DNA probe molecule with a predetermined sequence is hence respectively able to bind, i.e. hybridize, only a particular DNA strand, namely the one with the complementary sequence in each case.

If hybridization takes place, then, as can be seen from FIG. 2b, the value of the impedance between the electrodes 201 and 202 becomes modified. This modified impedance is determined by applying an AC voltage with an amplitude of approximately 50 mV to the electrode terminals 204, 205 and the resulting current by means of a connected measuring instrument (not shown).

In the event of hybridization, the capacitive component of the impedance between the electrodes 201, 202 is reduced. This is attributable to the fact that both the DNA probe molecules 206 and the DNA strands 208, which may hybridize with the DNA probe molecules 206 if appropriate, are nonconductive and therefore clearly shield the respective electrode 201, 202 electrically to a certain extent.

In order to improve the measurement accuracy, it is known from [4] to use a plurality of electrode pairs 201, 202 and to connect them in parallel, they being clearly arranged interdigitated with one another, so that a so-called interdigitated electrode 300 is obtained. The dimensioning of the electrodes and the distances between the electrodes are of the order of the length of the molecules to be detected, i.e. the DNA strand 208 or less, for example in the region of 200 nm and less.

[2] has disclosed a further procedure for analyzing the electrolyte with regard to the existence of a DNA strand with a predetermined sequence. In this procedure, the DNA strands with the desired sequence are marked, and the existence of the marked molecules is determined on the basis of their reflection properties. For this purpose, light in the visible wavelength region is radiated onto the electrolyte, and the light reflected by the electrolyte, in particular by the marked DNA strand which is to be detected, is recorded. The reflection characteristics, i.e. in particular the reflected light rays which are recorded, are used to determine whether or not the DNA strand which is to be detected and has the correspondingly predetermined sequence is present in the electrolyte.

This procedure is highly complex, since very precise knowledge of the reflection characteristics of the corresponding DNA strand is required and, furthermore, it is necessary to mark the DNA strands before the method commences. Furthermore, highly accurate alignment of the recording means for recording the reflected light beams is necessary, so that the reflected light beams can be recorded at all.

Therefore, this procedure is expensive, complicated and highly sensitive to disruptive influences and consequently the measurement result can very easily be distorted.

Furthermore, it is known from affinity chromatography (cf. [3]) to use immobilized low-molecular weight molecules, in particular ligands of high specificity and affinity, in order to specifically bind peptides and proteins, e.g. enzymes, in the analyte.

Furthermore, principles of a reduction/oxidation recycling process for recording macromolecular biopolymers are known from [5] and [6].

The reduction/oxidation recycling process, also referred to below as the redox recycling process, is explained in more detail below with reference to FIG. 4a to FIG. 4c.

FIG. 4a shows a biosensor 400 having a first electrode 401 and a second electrode 402, which are applied to a substrate 403 as insulator layer.

A holding region, configured as holding layer 404, is applied to the first electrode 401 made from gold. The holding region is used to immobilize DNA probe molecules 405 on the first electrode 401.

There is no such holding region on the second electrode.

If DNA strands with a sequence which is complementary to the sequence of the DNA probe molecules 405 are to be recorded by means of the biosensor 400, the sensor 400 is brought into contact with a solution 406 which is to be analyzed, for example an electrolyte, in such a manner that any DNA strands which are present in the solution 406 which is to be analyzed and have the complementary sequence to the sequence of the DNA probe molecules 405 can hybridize.

FIG. 4b shows the situation in which the DNA strands 407 which are to be recorded are present in the solution 406 which is to be analyzed and have hybridized with the DNA probe molecules 405.

The DNA strands 407 in the solution which is to be analyzed are marked with an enzyme 408, allowing molecules which are described below to be cleaved into part-molecules.

There is usually a considerably greater number of DNA probe molecules 405 than the number of DNA strands 407 to be determined which are present in the solution 406 which is to be analyzed.

After the DNA strands 407 which may be present in the solution 406 which is to be analyzed, having the enzyme 408, have hybridized with the immobilized DNA probe molecules 407, the biosensor 400 is rinsed, with the result that the unhybridized DNA strands are removed and the solution 406 which is to be analyzed is cleaned off the biosensor 400.

An electrically uncharged substance which contains molecules which can be cleaved by the enzyme at the hybridized DNA strands 407 into a first part-molecule with a negative first electric charge and a second part-molecule with a positive second electric charge is added to this rinsing solution which is used for rinsing or to a further solution which is supplied specifically for this purpose in a further phase.

As shown in FIG. 4c, the negatively charged part-molecules are attracted to the positively charged anode, as indicated by the arrow 411 in FIG. 4c.

The negatively charged first part-molecules 410 are oxidized at the first electrode 401, which as anode has a positive electrical potential, and as oxidized part-molecules 413 are attracted to the negatively charged cathode, i.e. the second electrode 402, where they are reduced again.

The reduced part-molecules 414 in turn migrate to the first electrode 401, i.e. to the anode.

In this way, an electric circuit current is generated, which is proportional to the number of charge carriers which are in each case generated by the enzymes 408.

The electrical parameter which is evaluated in this method is the change in the electric current $$\frac{dI}{dt}$$

a function of time t, as diagrammatically illustrated in diagram 500 in FIG. 5.

FIG. 5 shows the function of the electric current 501 as a function of time 502. The resulting curve 503 has an offset current $I_{offset}$ 504 which is independent of the time profile.

The offset current $I_{offset}$ 504 is generated by parasitic components on account of imperfections in the biosensor 400.

A significant cause of the offset current $I_{offset}$ 504 is that the coverage of the first electrode 401 with DNA probe molecules 405 is not completely dense.

In the case of a completely dense coverage of the first electrode 401 with DNA probe molecules 405, only purely capacitive electrical coupling would result on account of what is known as the double-layer capacitance formed by the immobilized DNA probe molecules 405 between the first electrode 401 and the electrically conductive solution 406 which is to be analyzed.

However, the incomplete coverage leads to parasitic current paths between the first electrode 401 and the solution 406 which is to be analyzed, and these paths have, inter alia, ohmic components.

In order, however, to allow the oxidation/reduction process to take place, the coverage of the first electrode 401 with the DNA probe molecules 405 must not be complete, so that the electrically charged part-molecules, i.e. the negatively charged first part-molecules, can be attracted to the first electrode 401 at all.

On the other hand, to achieve the highest possible sensitivity of a biosensor of this type, combined with low parasitic effects, the coverage of the first electrode 401 with DNA probe molecules 405 should be as dense as possible.

To achieve a high reproducibility of the measured values determined using a biosensor 400 of this type, both electrodes 401, 402 must always provide a sufficiently large surface area for the oxidation/reduction process as part of the redox recycling operation.

Therefore, in the biosensor according to the prior art, the result is a certain measurement unreliability in the detection of the DNA strands in a solution which is to be analyzed.

Therefore, the invention is based on the problem of detecting macromolecular biopolymers with increased accuracy during a redox recycling operation.

The problem is solved by the biosensor, the biosensor array and by the method for detecting macromolecular biopolymers using a biosensor having the features of the independent patent claims.

A biosensor has a first electrode, which has a holding region for holding probe molecules which can bind macromolecular biopolymers. Furthermore, the biosensor has a second electrode and a third electrode. The second electrode and the third electrode are designed in such a manner that the reduction/oxidation process takes place as part of a reduction/oxidation recycling operation at the second electrode and at the third electrode.

The result of this is that the reduction/oxidation process no longer has to take place at the first electrode, which is covered with the probe molecules.

This allows the first electrode to be covered with a considerably greater density of probe molecules, with the result that the parasitic effects described above are avoided during detection of the changing current through the biosensor.

A biosensor array may include a multiplicity of first electrodes, which each have a holding region for holding probe molecules which can bind macromolecular biopolymers. Furthermore, a multiplicity of second electrodes and a multiplicity of third electrodes are provided. In each case, the second electrodes and the third electrodes are designed in such a manner that the reduction/oxidation process takes place as part of the redox recycling operation at the second electrodes and at the third electrodes.

In a method for detecting macromolecular biopolymers using a biosensor, a biosensor having a first electrode, which has a holding region for holding probe molecules which can bind macromolecular biopolymers, and a second electrode and a third electrode, is used.

A solution which is to be analyzed is brought into contact with the biosensor. The solution may contain the macromolecular biopolymers which are to be recorded. If the macromolecular biopolymers are present in the solution which is to be analyzed, they bind to the probe molecules which have been immobilized on the holding region of the first electrode and can in each case bind the macromolecular biopolymers. The bound macromolecular biopolymers have been or are marked with an enzyme, for example after binding has taken place, for example after hybridization of the DNA strands has taken place.

In a further step, the biosensor is rinsed with a rinsing solution, so that the solution which is to be analyzed and therefore unhybridized, i.e. unbound macromolecular biopolymers, are removed from the biosensor.

In a further step, a further solution, which may also be formed by adding a substance to the rinsing solution, is brought into contact with the biosensor.

The further solution contains molecules which can be cleaved by the enzyme at the macromolecular biopolymers.

In each case one cleavable molecule is cleaved into a first part-molecule having a first charge and a second part-molecule having a second electric charge. The first part-molecule is oxidized or reduced at the third electrode, and the oxidized or reduced first part-molecule is reduced or oxidized at the second electrode, so that a redox recycling operation is carried out between the third electrode and the second electrode.

The macromolecular biopolymers are determined as a function of the redox recycling operation, i.e., for example as in the prior art, the profile of the circuit current of the redox recycling operation is determined, and from this the number of bound macromolecular biopolymers on the first electrode is determined.

If large numbers of DNA strands which have been marked or are yet to be marked with the enzyme hybridize with the immobilized DNA probe molecules in a small area, there is a correspondingly high concentration of these enzymes at this region, and the rate of increase of the circuit current generated is higher than in another region, where fewer DNA strands which have been marked with the enzyme are hybridized. By comparing the rates of increase between various regions of the biosensor, it is in this way possible to determine not only whether DNA strands are hybridizing in the solution which is to be analyzed with the DNA probe molecules of a predetermined sequence, but also how well, i.e. with what level of efficiency, this hybridization takes place compared to other DNA probe molecules.

In other words, a biosensor of this type supplies qualitative and quantitative information concerning the DNA content of a solution to be analyzed.

The enzyme used may, by way of example, be an enzyme belonging to the class of the NADH-independent dehydrogenases or an enzyme belonging to the class of the phenoloxidases.

The concentration of the reduction/oxidation process at the second electrode and the third electrode can be ensured, for example, by the first electrode having a first electrical potential, the second electrode having a second electrical potential and the third electrode having a third electrical potential. In this case, the third electrical potential can be selected in such a manner that during the redox recycling operation the reduction or oxidation takes place only at the second and third electrodes.

According to one configuration of the invention, this is achieved by the fact that the third electrical potential is greater than the first electrical potential, and that the first electrical potential is greater than the second electrical potential.

The holding region of the first electrode may be coated with a material which can immobilize probe molecules.

The holding region may therefore include, by way of example, one of the following materials:
  hydroxyl radicals,
  epoxy radicals,
  amine radicals,
  acetoxy radicals,
  isocyanate radicals,
  succinimidyl ester radicals,
  thiol radicals,
  gold,
  silver,
  platinum,
  titanium.

The holding region may be designed both to hold ligands to which peptides or proteins can be bound and to hold DNA probe molecules to which DNA molecules can be bound.

The electrodes may be arranged in an interdigitated electrode arrangement, as described for example in [4], the third electrode in each case being arranged between the first and the second electrodes.

According to a further configuration of the invention, the electrodes are arranged in circular form concentrically around one another, the third electrode in each case being arranged between the first electrode and the second electrode.

Furthermore, the first electrode and the second electrode and/or the third electrode may be arranged in such a manner relative to one another that between the first electrode and the second electrode and/or the third electrode they can form substantially uncurved field lines of an electric field which is generated between the first electrode and the second electrode and/or the third electrode.

The term macromolecular biopolymers is to be understood, by way of example, as meaning proteins or peptides or DNA strands of in each case a predetermined sequence.

Irrespective of which type of macromolecular biopolymer is to be recorded in the solution which is to be analyzed, the macromolecular biopolymer can be marked in advance by the enzyme.

If proteins or peptides are to be recorded as macromolecular biopolymers, the immobilized molecules are ligands, for example active substances with a possible binding activity which bind the proteins or peptides which are to be recorded to the respective electrode on which the corresponding ligands are arranged.

Suitable ligands are enzyme agonists or enzyme antagonists, pharmaceuticals, sugars or antibodies or any molecule which has the ability to specifically bind proteins or peptides.

If DNA strands of a predetermined sequence are used as macromolecular biopolymers which are to be recorded by means of the biosensor, the biosensor can be used to hybridize DNA strands of a predetermined sequence to DNA probe molecules which have a complementary sequence to the sequence of the immobilized DNA strands, as molecules on the first electrode.

In the context of the present description, the term probe molecule is to be understood as meaning both a ligand and a DNA probe molecule.

The holding region may be designed to hold probe molecules to which peptides or proteins can be bound.

Alternatively, the holding region may be designed to hold DNA probe molecules to which DNA molecules can be bound.

An exemplary embodiment of the invention is illustrated in the figures and is explained in more detail below. In the drawing.

Figure 12A:
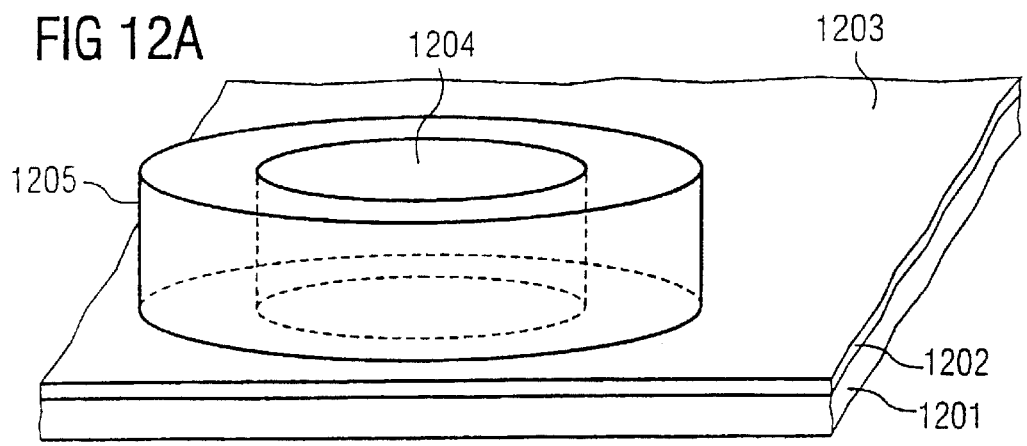
Figure 12B:
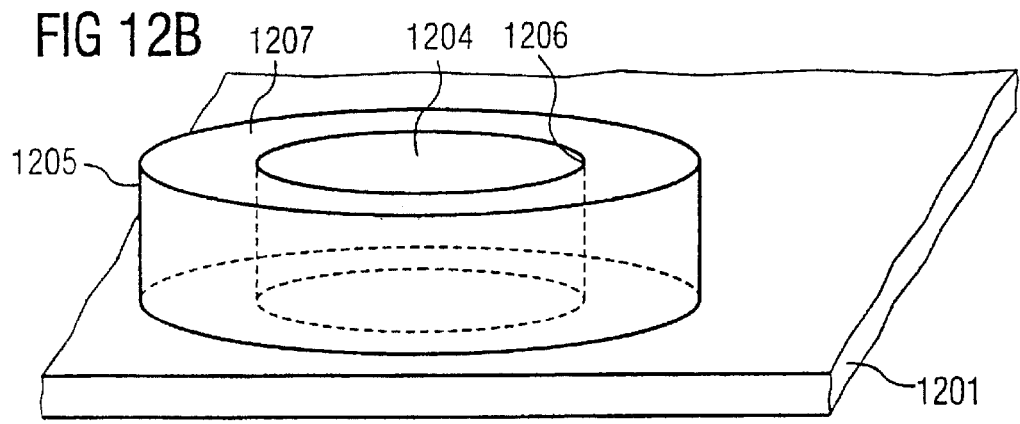
Figure 12C:
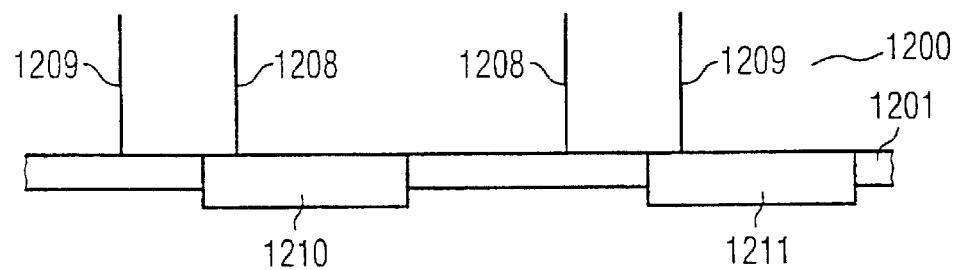
Figure 13:
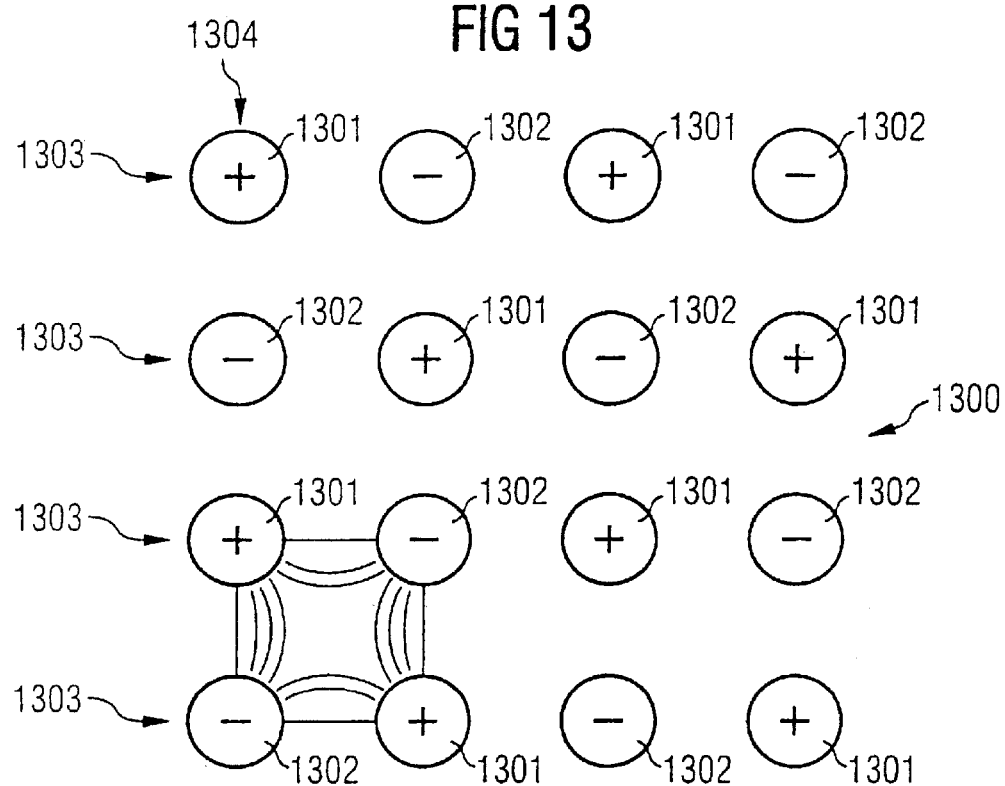
Figure 14:
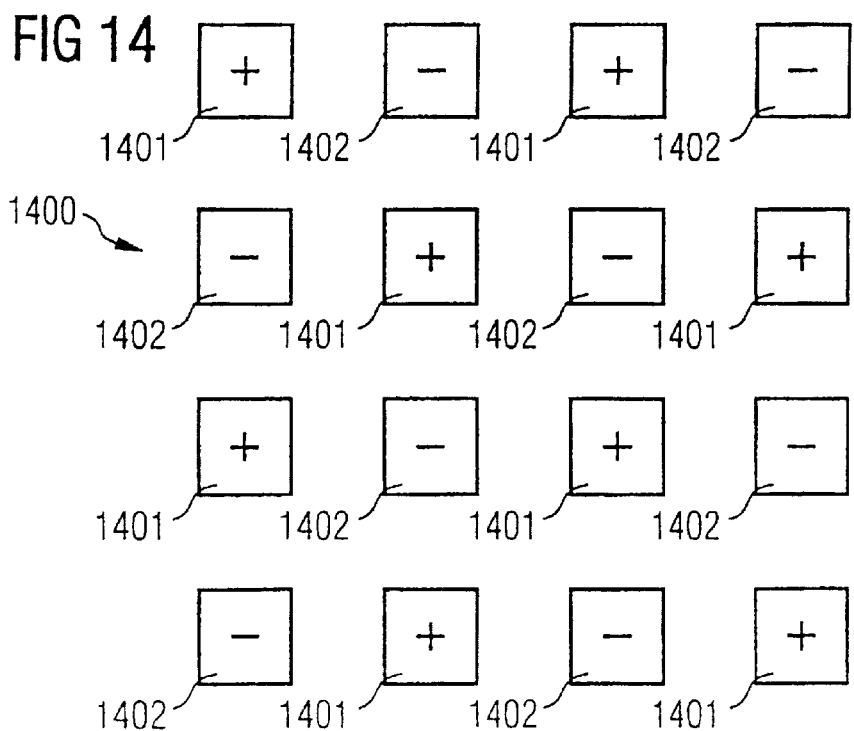
Figure 15:
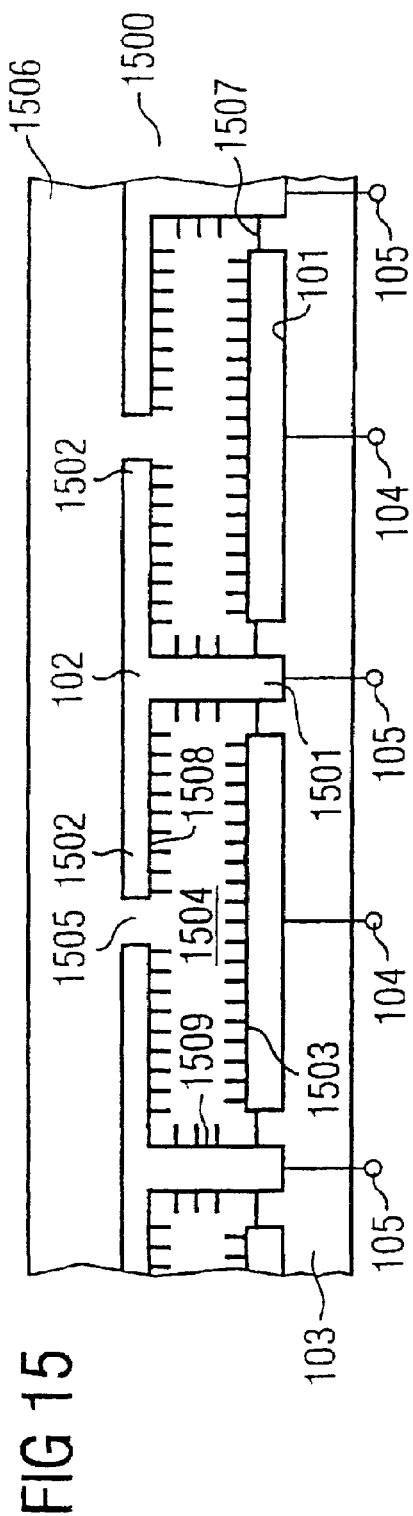
Figure 16:
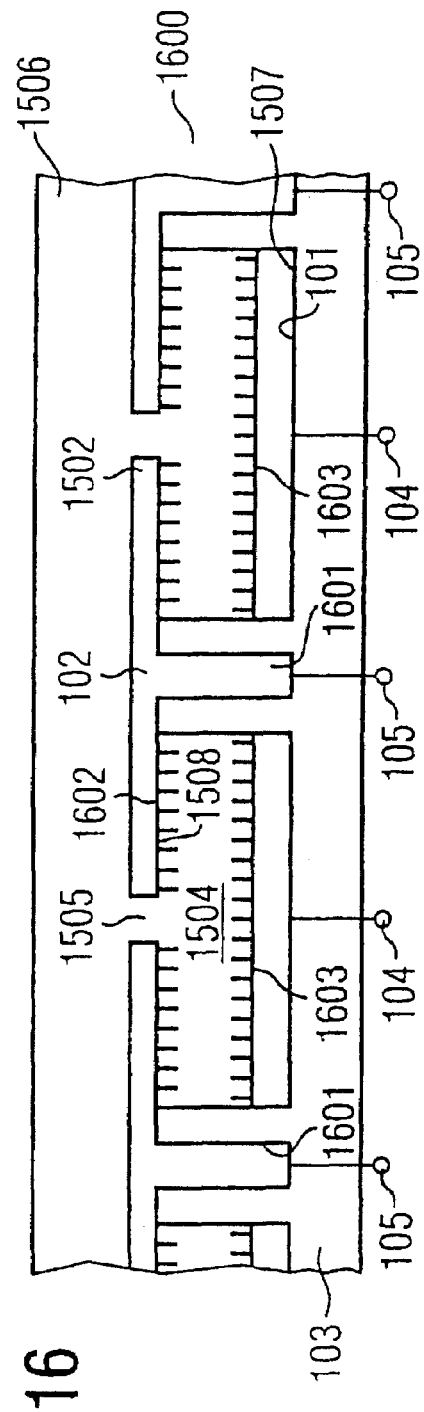
Figure 18:
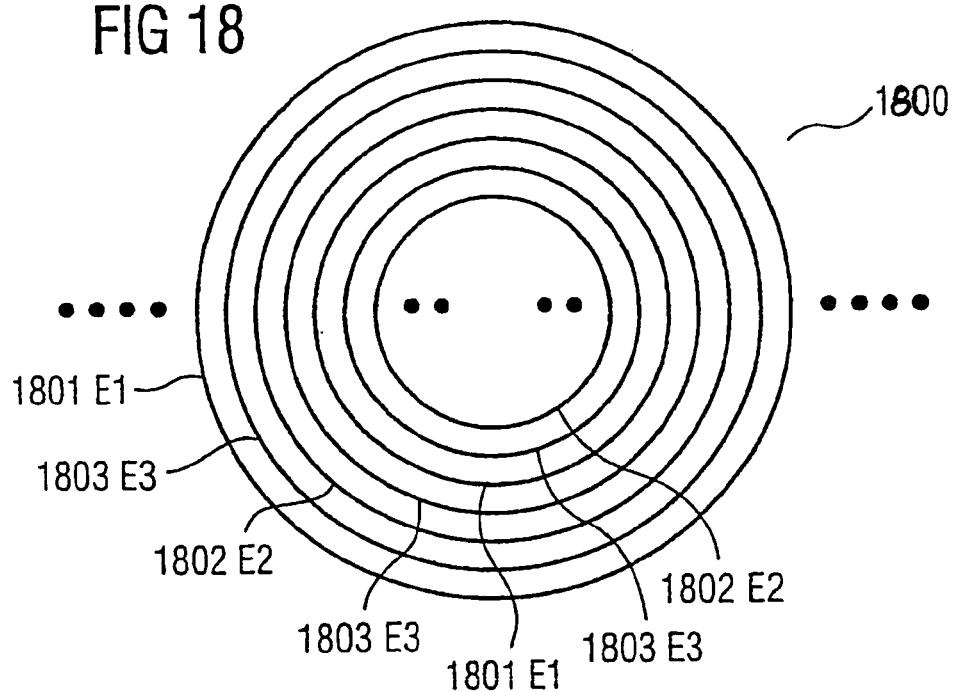
Figure 19:
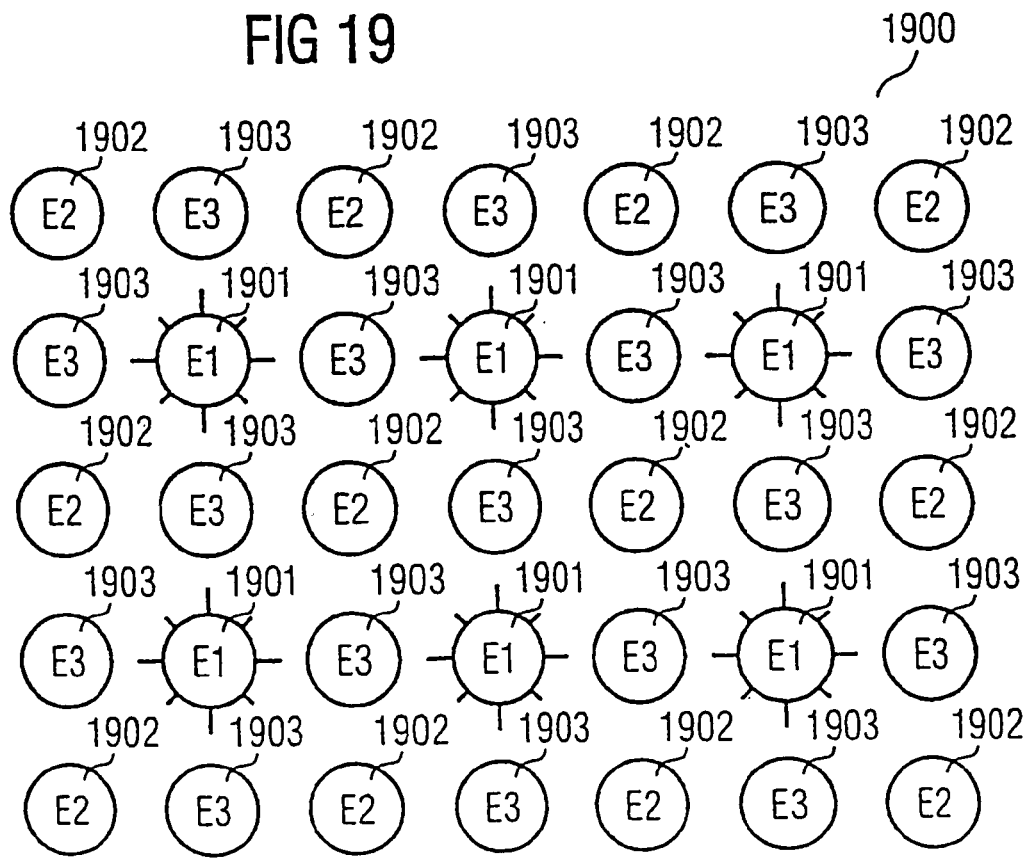

FIGS. 12a to 12c respectively show a cross section through a biosensor at various times during the production method in accordance with a further exemplary embodiment of the invention;

FIG. 13 shows a plan view of a biosensor array according to an exemplary embodiment of the invention with cylindrical electrodes;

FIG. 14 shows a plan view of a biosensor array in accordance with an exemplary embodiment of the invention with cuboidal electrodes;

FIG. 15 shows a cross-sectional view through a biosensor in accordance with a further exemplary embodiment of the invention;

FIG. 16 shows a cross-sectional view through a biosensor in accordance with a further exemplary embodiment of the invention; and FIGS. 17a to 17g show cross-sectional views through a biosensor during individual method steps of a production method according to a further exemplary embodiment of the invention;

FIG. 18 shows a further electrode arrangement in accordance with a further exemplary embodiment of the invention;

FIG. 19 shows a plan view of a biosensor array in accordance with an exemplary embodiment of the invention with cuboidal electrodes, in which the electrodes are illustrated with the electrical potential which is respectively assigned to them.

Figure 1:
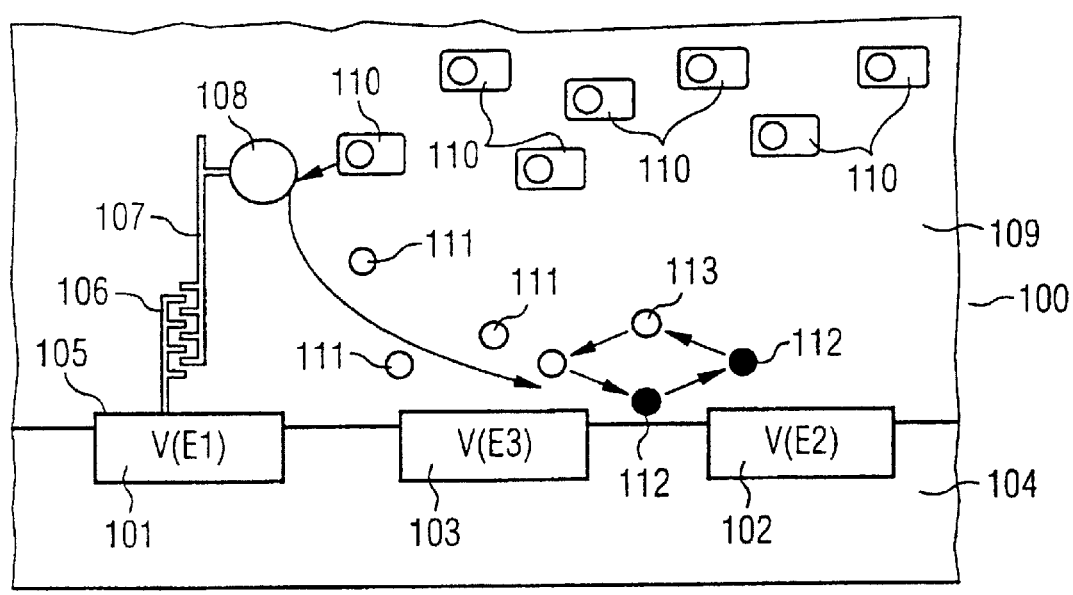
FIG. 1 shows a sketch of a biosensor in accordance with an exemplary embodiment of the invention.
Figure 2A:
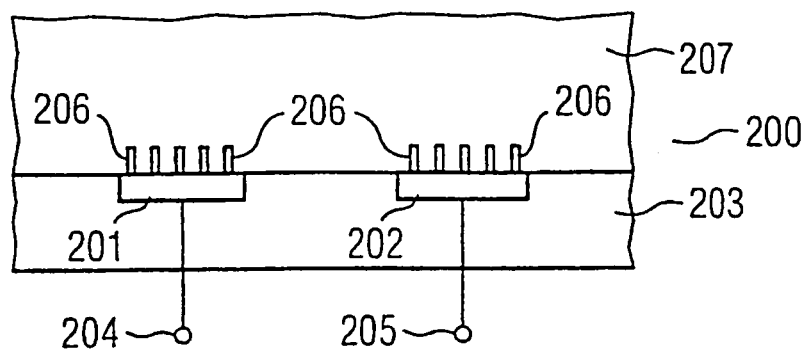
FIGS. 2a and 2b show a sketch of two planar electrodes, by means of which the existence of DNA strands which are to be recorded in an electrolyte (FIG. 2a) or their nonexistence (FIG. 2b) can be detected.
Figure 2B:
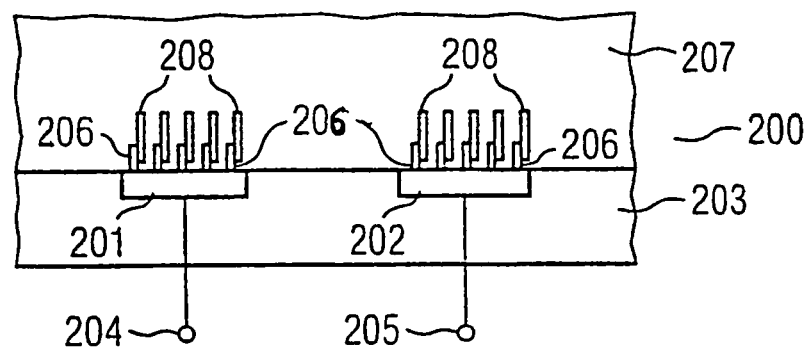
Figure 3:
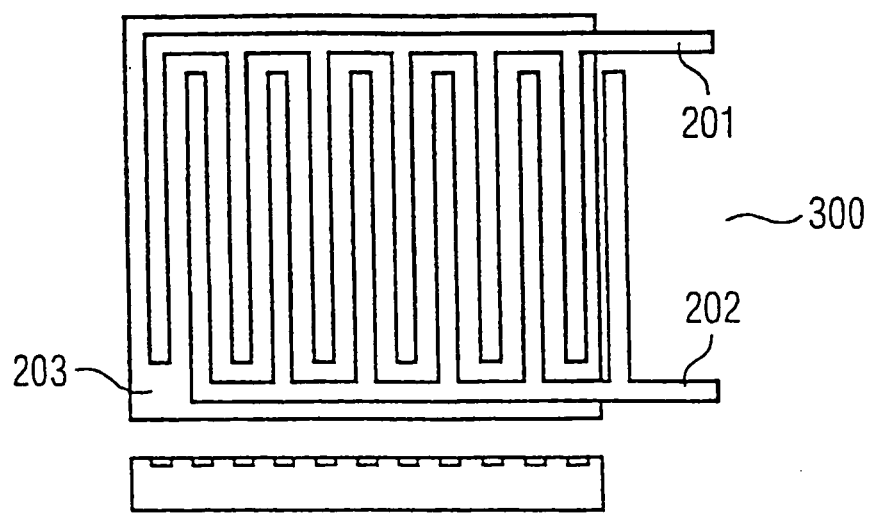
FIG. 3 shows interdigitated electrodes according to the prior art.
Figure 4A:
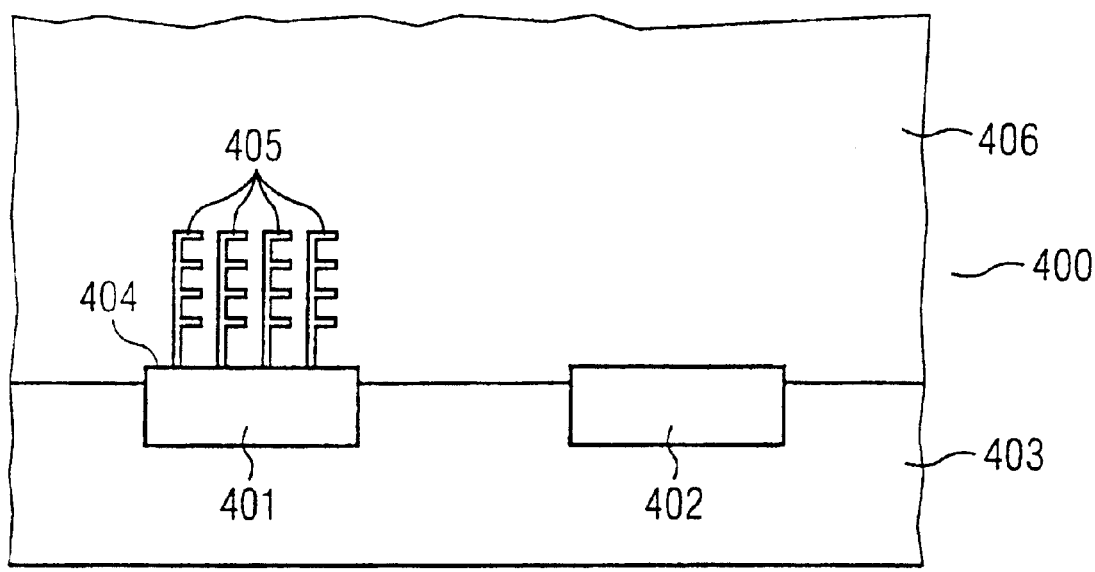
FIGS. 4a to 4c show sketches of a biosensor in accordance with the prior art, on the basis of which individual states as part of the redox recycling operation are explained.
Figure 4B:
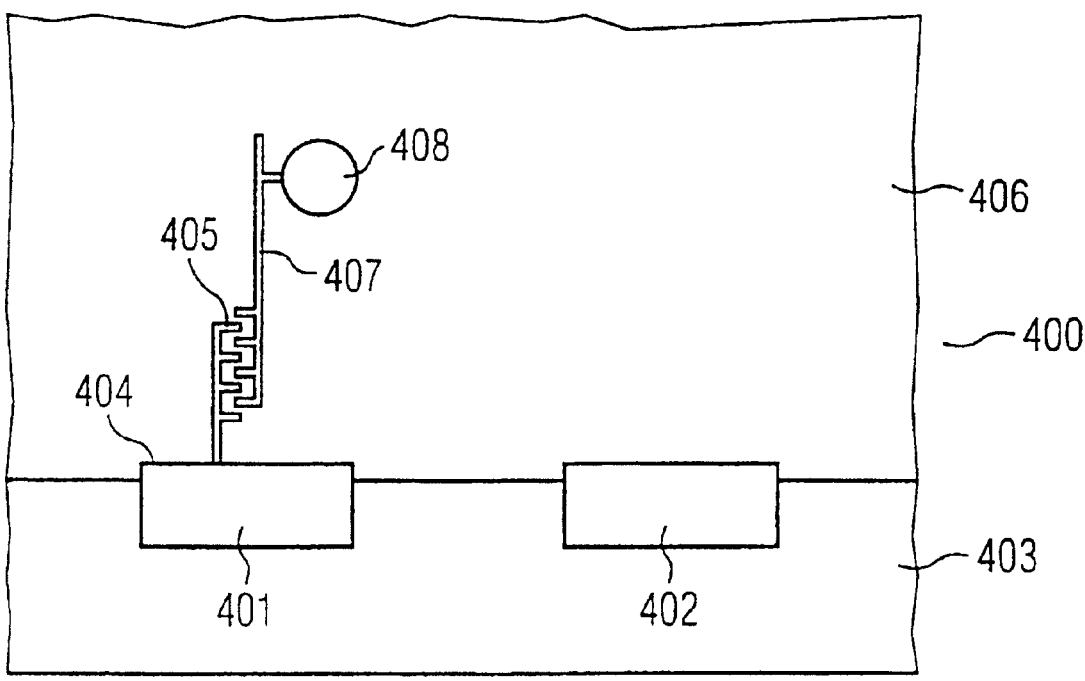
Figure 4C:
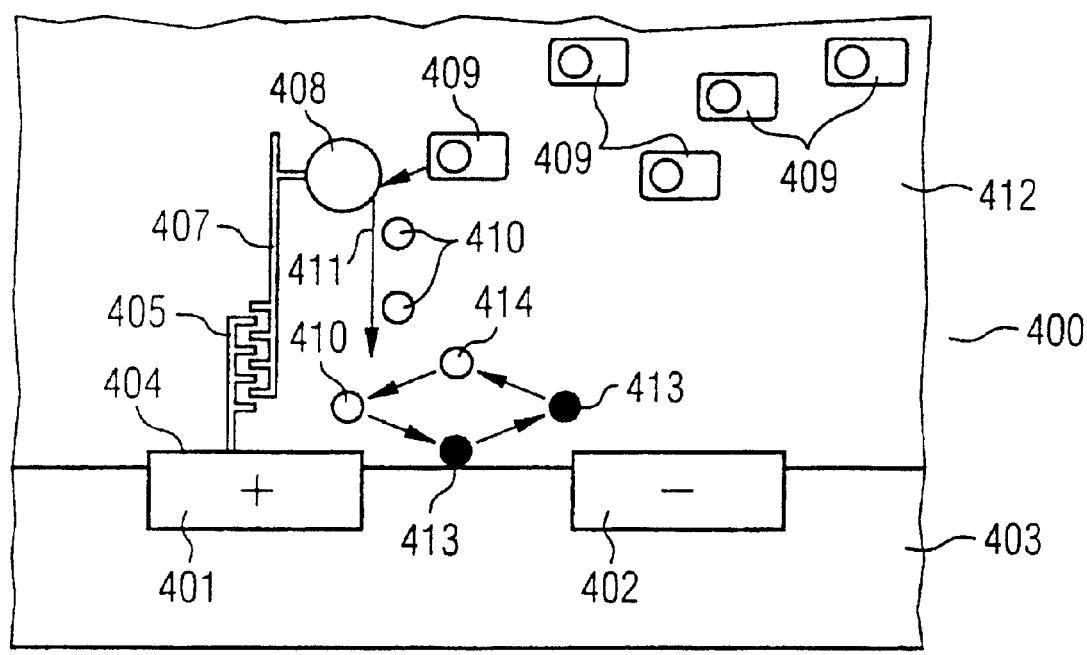
Figure 5:
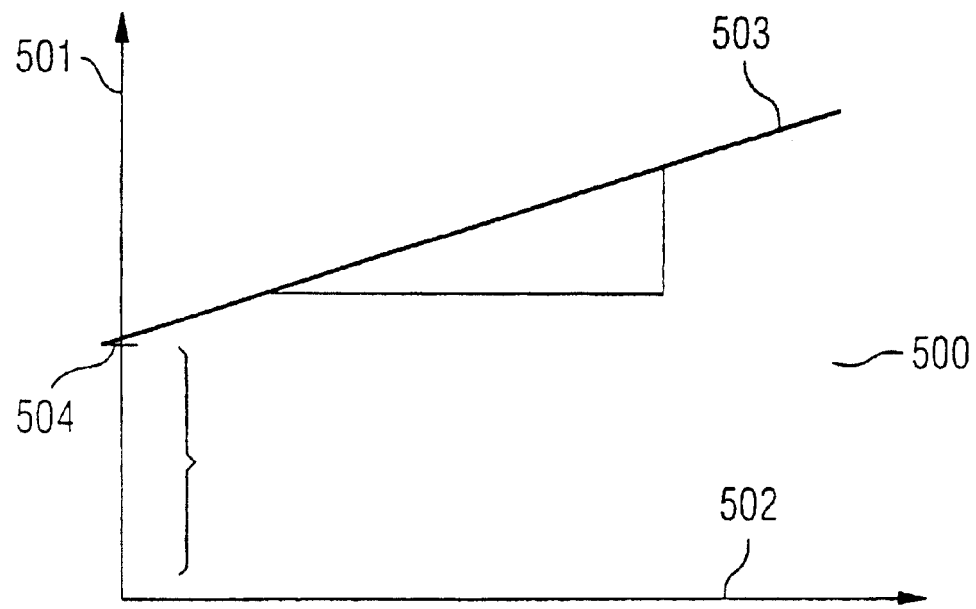
FIG. 5 shows a functional curve of a circuit current in accordance with the prior art as part of a redox recycling operation.

FIG. 1 shows a biosensor 100 in accordance with an exemplary embodiment of the invention.

The biosensor 100 has three electrodes, namely a first electrode 101, a second electrode 102 and a third electrode 103.

The electrodes 101, 102, 103 are electrically insulated from one another by means of an insulator material as insulator layer 104.

On the first electrode 101 there is a holding region 105 for holding probe molecules which can bind macromolecular biopolymers.

According to this exemplary embodiment, the probe molecules 106, which are immobilized at the holding region, are DNA probe molecules, with which DNA strands having a sequence which is complementary to the sequence of the DNA probe molecules can hybridize.

The DNA probe molecules 106 are immobilized at the first electrode 101, which is made from gold, by means of the known gold-sulfur coupling. When a different material is used to bind the probe molecules, the material is provided with the appropriate coating material, on which the probe molecules can be immobilized.

During the immobilization of the DNA probe molecules on the first electrode 101, different electrical potentials are applied to the electrodes, so that an electrical field is formed between the electrodes, in such a manner that immobilization of the DNA probe molecules is possible only at the first electrode 101 and is prevented at the second electrode 102 and/or at the third electrode 103.

In a first step, in a similar manner to the method according to the prior art, as has been described above, a solution which is to be analyzed, for example an electrolyte, containing the macromolecular biopolymer which is to be recorded if present, i.e. the DNA strands which can be hybridized by the DNA probe molecules, is brought into contact with the biosensor 100, i.e. in particular with the first electrode 101 with the DNA probe molecules 106. This takes place in such a manner that any DNA strands which are present in the solution which is to be analyzed can hybridize with the DNA probe molecules.

After the hybridization has taken place, the biosensor 100 is rinsed by means of a rinsing solution (not shown), i.e. the unhybridized DNA strands and the solution to be analyzed are removed.

In a further step, a further solution 109 is brought into contact with the biosensor 100, in particular with the first electrode 101.

FIG. 1 shows the biosensor 100 in the state in which DNA strands 107 have already hybridized with the DNA probe molecules 106. The hybridized DNA strands 107 are each marked with an enzyme 108, with which molecules explained below can be cleaved in the further solution 109.

According to the present exemplary embodiment, by way of example the following can be used as enzyme 108:
a-galactosidase,
b-galactosidase,
b-glucosidase,
a-mannosidase,
alkaline phosphatase,
acidic phosphatase,
oligosaccharide dehydrogenase,
glucose dehydrogenase,
laccase,
tyrosinase,
or enzymes of related types.

It should be noted that low-molecular weight enzymes are able to ensure the highest conversion efficiency and therefore also the highest sensitivity.

Therefore, the further solution 109 contains molecules 110 which can be cleaved by the enzyme 108 into a first part-molecule 111 with a negative electric charge and a second part-molecule with a positive electric charge.

By way of example, in particular the following can be used as the cleavable molecule 110:
p-aminophenyl hexopyranosides,
p-aminophenyl phosphates,
p-nitrophenyl hexopyranosides,
p-nitrophenyl phosphates, or
suitable derivatives of
 a) diamines,
 b) catecholamines,
 c) $Fe(CN)_{4-}^{6}$,
 d) ferrocene,
 e) dicarboxylic acid,
 f) ferrocenelysine,
 g) osmium bipyridyl NH, or
 h) PEG-ferrocene$^2$.

An electrical potential is applied to each of the electrodes 101, 102, 103.

Therefore, a first electrical potential $V(E1)$ is applied to the first electrode 101, a second electrical potential $V(E2)$ is applied to the second electrode 102, and a third electrical potential $V(E3)$ is applied to the third electrode 103.

During the actual measurement phase, which in principle takes place in a similar manner to the procedure which is known from the prior art, as has been described above, a potential drop, which in each case follows as a function of the sign of the charge, of the electrical potentials is applied to the electrodes 101, 102, 103, in such a manner that the following relationship applies:

$V(E3) > V(E1) > V(E2)$.

If, by way of example, the third electrode 103 has a positive electric potential V(E3), the third electrode 103 has the highest electric potential of the electrodes 101, 102, 103 of the biosensor 100.

The result of this is that the first part-molecules 111 produced, with a negative charge on account of the highest electric potential V(E3), which is present at the third electrode 103, is attracted to the positively charged third electrode 103 and no longer, as in the prior art, to the first electrode 101.

According to the invention, the first electrode 101 is now no longer used both as holding electrode for holding the probe molecules and as measuring electrode for oxidizing or reducing the respective part-molecules.

The function of the electrode at which the oxidation or reduction of the part-molecules produced takes place is now obviously taken over by the third electrode 103.

This obviously means that by means of the third electrode 103 the first electrode 101 is shielded from the cleaved part-molecules.

In this way, the coverage of the first electrode with the DNA probe molecules 106 can be increased considerably.

Oxidation of the negatively charged part-molecules 111 takes place at the third electrode 103, and the oxidized first part-molecules 112 are attracted to the second electrode 102, since the latter have the lowest electrical potential V(E2) of all the electrodes 101, 102, 103 in the biosensor 100.

The oxidized part-molecules are reduced at the second electrode 102, and the reduced part-molecules 113 are in turn attracted to the third electrode 103, where oxidation takes place once again.

This in turn results in a circuit current which is recorded in a known way, resulting in a profile of the circuit current over the course of time, from which, in turn, the number of hybridized DNA strands 107 with the enzyme 108 as marker can be determined on the basis of the proportional relationship between the circuit current and the number of charge carriers produced by the enzyme 108.

Figure 6:
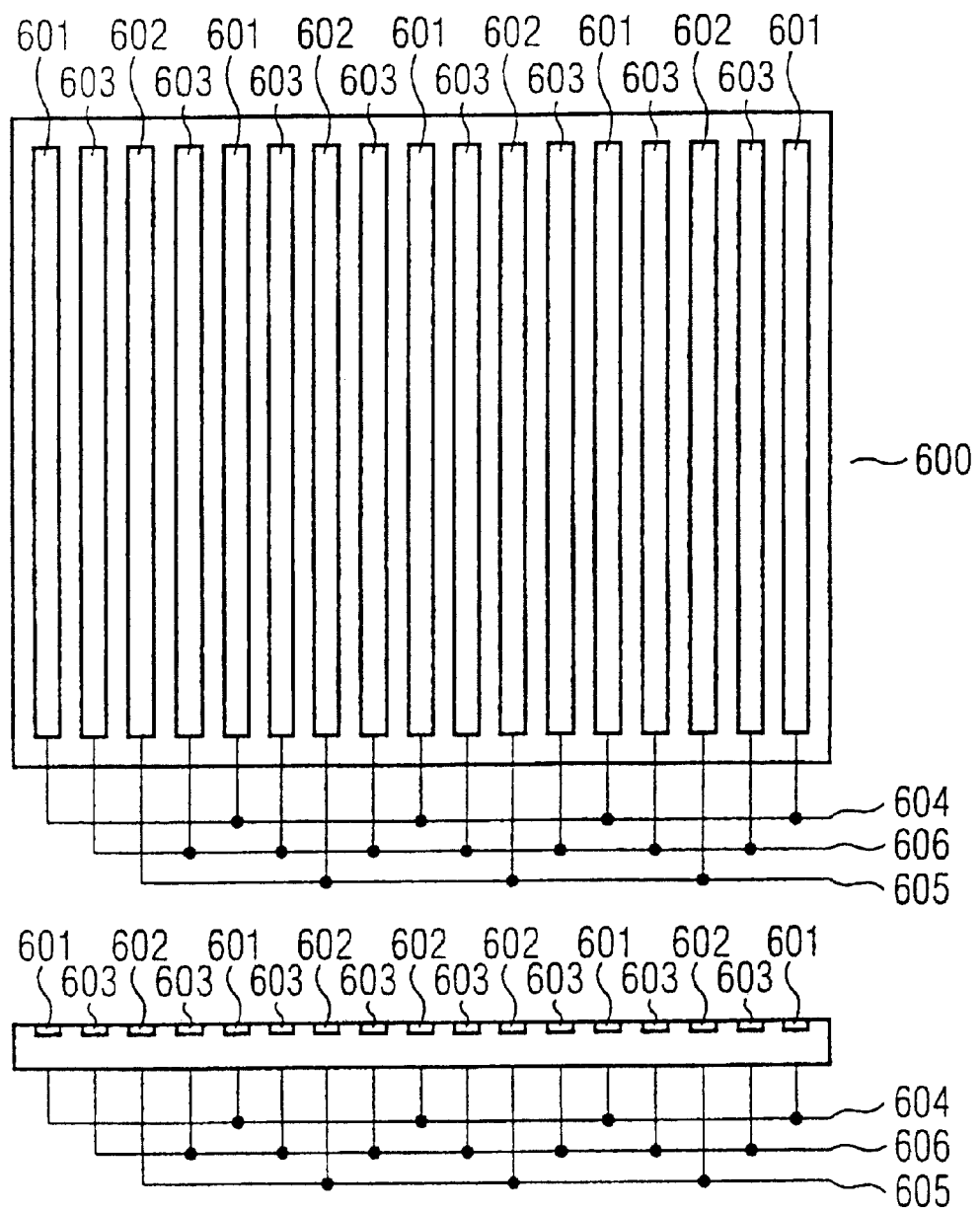
FIG. 6 shows an interdigitated electrode arrangement in accordance with an exemplary embodiment of the invention.

An alternative embodiment to the biosensor 100 is illustrated in FIG. 6. According to a second exemplary embodiment, the electrodes at a biosensor 600 may be arranged as interdigitated electrodes, in which case the third electrode 603 is in each case arranged between the first electrode 601 and the second electrode 602.

The first electrodes 601, the second electrodes 602 and the third electrodes 603 are in each case connected in parallel and are respectively coupled to a first electrical connection 604, a second electrical connection 605 and a third electrical connection 606.

Obviously, what this means is that in the interdigitated electrode arrangement 600 the first electrode 601, on which the holding region for holding probe molecules is in each case arranged, is once again shielded with respect to the redox recycling operation.

Furthermore, it should be noted that the invention is not restricted to the detection of DNA strands, but rather it is in general terms possible to detect macromolecular biopolymers; if proteins or peptides are to be detected, the probe molecules are designed as ligands which can bind to the proteins or peptides.

Furthermore, the biosensor 100, 600 can be used in a biosensor array having a multiplicity of biosensors of this type.

Each point which, as electrode, forms an element of the biosensor array has the property described above. It merely needs to be ensured that the first electrode, at which probe molecules in each case are or can be immobilized, is electrically shielded from the cleaved part-molecules.

Therefore, it can also be seen that a different number of electrodes, which correspond to the first electrode 101, the second electrode 102 and the third electrode 103 in accordance with the exemplary embodiment from FIG. 1, may also be distributed with a different density over a biosensor, provided that it is ensured that the first electrode is shielded from the cleaved part-molecules as part of the redox recycling operation.

Furthermore, in a biosensor array, the measurement may be carried out as a function of locally varying electrode potentials. Different density distributions of the functionally different electrodes are also possible within the context of a biosensor array.

Figure 7:
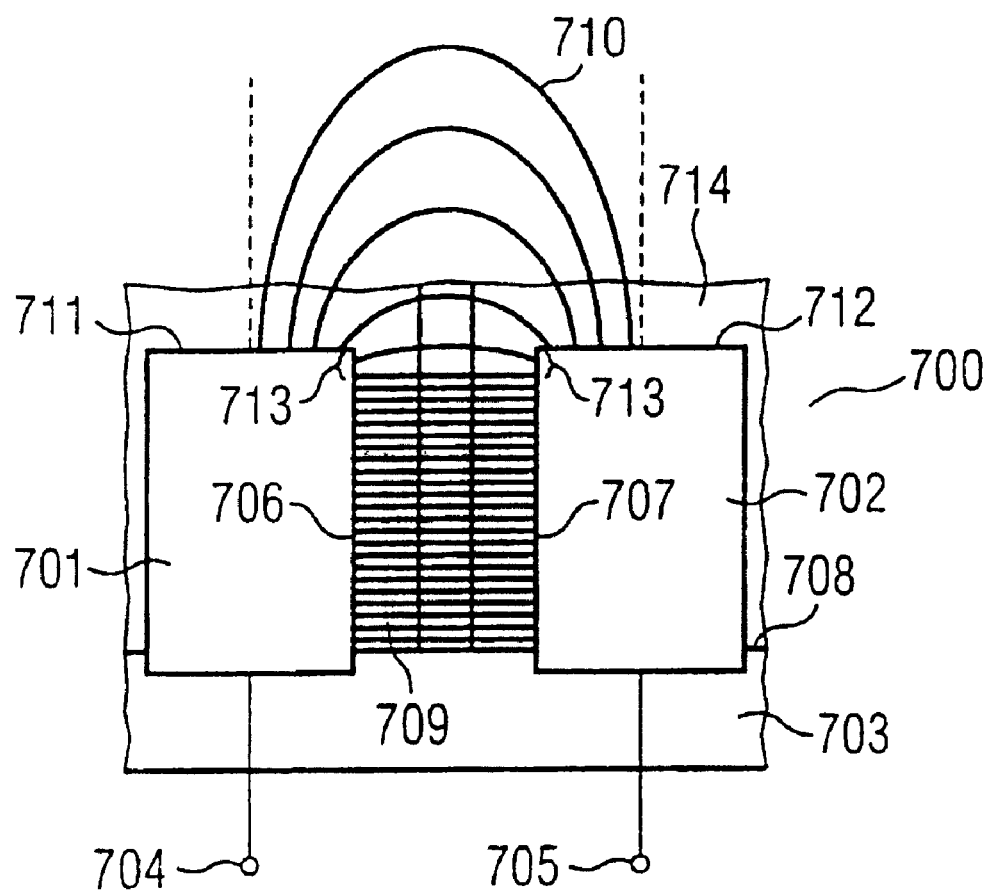
FIG. 7 shows a biosensor in accordance with an exemplary embodiment of the invention.

FIG. 7 shows a biosensor chip 700 with a further electrode configuration.

The biosensor chip 700 has a first electrode 701 and a second electrode 702, which are arranged on an insulator layer 703 in such a way that the first electrode 701 and the second electrode 702 are electrically insulated from one another.

The first electrode 701 is coupled to a first electrical terminal 704, and the second electrode 702 is coupled to a second electrical terminal 705.

The electrodes 701, 702 have a cuboid structure, with a first electrode face 706 of the first electrode 701 and a first electrode face 707 of the second electrode 702 facing one another while being aligned essentially parallel.

This is achieved, according to this exemplary embodiment, by the fact that the electrodes 701, 702 have side walls 706, 707 which are essentially perpendicular with respect to the surface 708 of the insulator layer 703, and which respectively form the first electrode face 706 of the first electrode 701 and the first electrode face 707 of the second electrode 702.

If an electric field is applied between the first electrode 701 and the second electrode 702, then owing to the electrode faces 706, 707 which are aligned essentially parallel with one another, a field line profile is produced with field lines 709 which are essentially uncurved between the faces 706, 707.

Curved field lines 710 occur only between a second electrode face 711 of the first electrode 701 and a second electrode face 712 of the second electrode 702, which respectively form the upper surfaces for the electrodes 701, 702, as well as in an edge region 713 between the electrodes 701, 702.

The first electrode faces 706, 707 of the electrodes 701, 702 are formed as holding regions for holding probe molecules, which can bind macromolecular biopolymers that are detected by means of the biosensor 700.

The electrodes 701, 702 are made of gold according to this exemplary embodiment.

Covalent bonds are produced between the electrodes and the probe molecules, the sulfur for forming a gold-sulfur coupling being present in the form of a sulfide or a thiol.

For the case in which DNA probe molecules are used as the probe molecules, such sulfur functionalities are part of a modified nucleotide which is incorporated by means of phosphoramidite chemistry during an automated DNA synthesis method at the 3' end or at the 5' end of the DNA strand to be immobilized. The DNA probe molecule is therefore immobilized at its 3' end or at its 5' end.

For the case in which ligands are used as the probe molecules, the sulfur functionalities are formed by one end of an alkyl linker or of an alkylene linker, the other end of which has a chemical functionality suitable for the covalent bonding of the ligand, for example a hydroxyl radical, an acetoxy radical or a succinimidyl ester radical.

The electrodes, i.e. in particular the holding regions, are covered during measurement use with an electrolyte 714, in general with a solution to be analyzed.

If the solution 714 to be analyzed contains the macromolecular biopolymers to be recorded, for example DNA strands to be recorded which have a predetermined sequence and which can hybridize with the immobilized DNA probe molecules on the electrodes, then the DNA strands hybridize with the DNA probe molecules.

If the solution 714 to be analyzed does not contain any DNA strands with the sequence complementary to the sequence of the DNA probe molecules, then no DNA strands from the solution 714 to be analyzed can hybridize with the DNA probe molecules on the electrodes 701, 702.

As has been explained above, a redox recycling operation is started between the electrodes 701, 702, and in this way the number of marked hybridized DNA strands, generally of the marked, bound macromolecular biopolymers, is determined.

Figure 8:
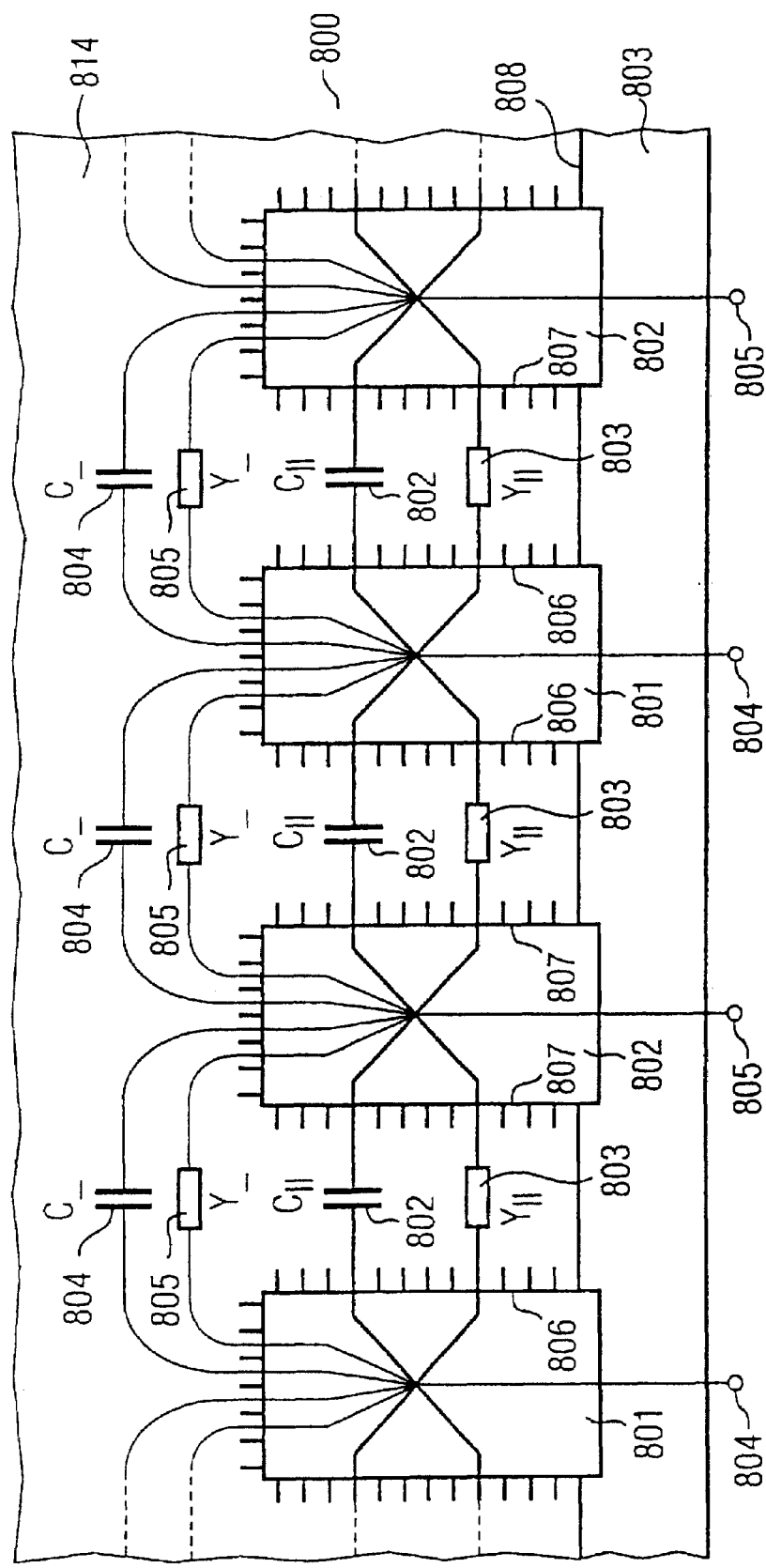
FIG. 8 shows a cross section through a biosensor with two electrodes which are arranged as an interdigitated electrode arrangement.

FIG. 8 shows a biosensor 800 with a further electrode configuration according to a further exemplary embodiment of the invention.

In the biosensor 800, in the same way as in the biosensor 700 according to the exemplary embodiment shown in FIG. 7, two electrodes 701, 702 are provided which are applied on the insulator layer 703.

In contrast to the biosensor 700 with only two cuboid electrodes, the two electrodes according to the biosensor 800 represented in FIG. 8 are arranged as a plurality of respectively alternately arranged, parallel-connected electrodes in the form of the known interdigitated electrode arrangement.

For further illustration, FIG. 8 also shows a schematic electrical equivalent circuit diagram, which is indicated in the representation of the biosensor 800.

Since essentially uncurved field lines occur with respect to the surface 708 of the insulator layer 703 between the electrode faces 706, 707 of the electrodes 701, 702, which face one another while being essentially parallel, as was represented in FIG. 7, the component of the first capacitance 802 and of the first admittance 803 produced by the uncurved field lines predominates compared with the second capacitance 804 and the second admittance 805, which are produced by the curved field lines 710.

This significantly greater component of the first capacitance 802 and of the first admittance 803 in relation to the total admittance, which is obtained from the sum of the first capacitance 802 and the second capacitance 804 as well as the first admittance 803 and the second admittance 805, has the effect of significantly increasing the sensitivity of the biosensor 800 when the state of the biosensor 800 changes, i.e. when DNA strands in the solution 714 to be analyzed hybridize with DNA probe molecules 801 immobilized on the holding regions on the electrode faces 706, 707.

Clearly, with the same lateral dimensions of the electrodes 701, 702 and the same dimensions of the previously introduced active region, i.e. with the same area of the holding regions on the electrode faces, a substantially greater component of field lines of an applied electric field between the electrodes 701, 702 is therefore contained in the volume in which the hybridization takes place when DNA strands to be recorded are contained in the solution 714 to be analyzed, than in the case of a planar electrode arrangement.

In other words, this means that the capacitance of the arrangement according to the invention per unit chip area is significantly greater than the capacitance per unit chip area in the case of a planar electrode arrangement.

A few alternative possibilities for producing a cuboid sensor electrode with essentially vertical side walls will be explained below.

Figure 9A:
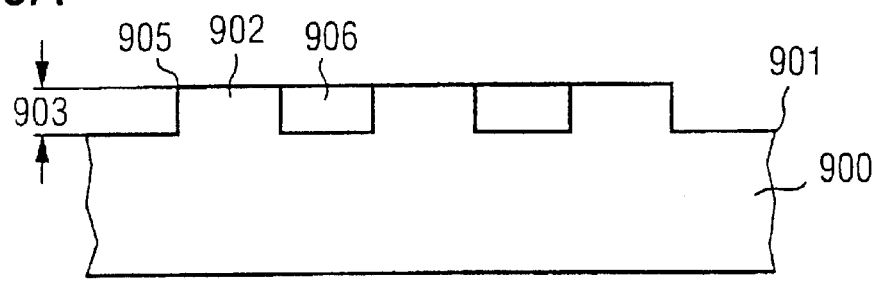
FIGS. 9a to 9d show cross-sectional views through an interdigitated electrode in four method steps in a method for producing a biosensor in accordance with an exemplary embodiment of the invention.

First Method for Producing Metal Electrodes with Essentially Vertical Side Walls, Which Can Immobilize Probe Molecules FIG. 9a shows a silicon substrate 900, as is produced for known CMOS processes.

On the silicon substrate 900, which already contains integrated circuits and/or electrical terminals for the electrodes to be formed, an insulator layer 901 which is also used as a passivation layer is applied with a sufficient thickness, with a thickness of 500 nm according to the exemplary embodiment, by means of a CVD method.

The insulator layer 901 may be made of silicon oxide $SiO_2$ or silicon nitride $Si_3N_4$.

The interdigitated arrangement of the biosensor 800 according to the exemplary embodiment described above is defined by means of photolithography on the insulator layer 901.

By means of a dry etching method, e.g. reactive ion etching (RIE), steps 902 are subsequently produced, i.e. etched, in the insulator layer 901 with a minimum height 903 of approximately 100 nm according to the exemplary embodiment.

The height 903 of the steps 902 must be large enough for a subsequent self-aligning process to form the metal electrode.

It should be pointed out that an evaporation coating method or a sputtering method may alternatively also be used for applying the insulator layer 901.

During the structuring of the steps 902, care should be taken that the flanks of the steps 902 are steep enough so that they form sufficiently sharp edges 905. An angle 906 of the step flanks, measured with respect to the surface of the insulator layer 901, should be at least 50 degrees according to the exemplary embodiment.

Figure 9B:
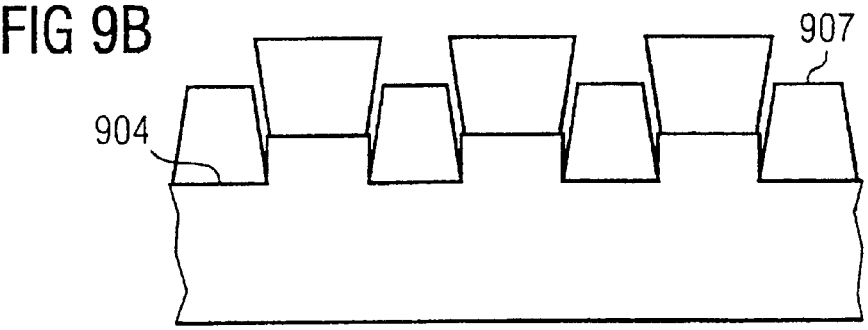
Figure 9C:
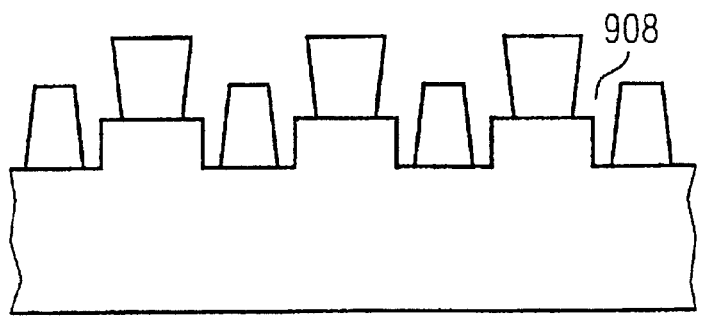
Figure 9D:
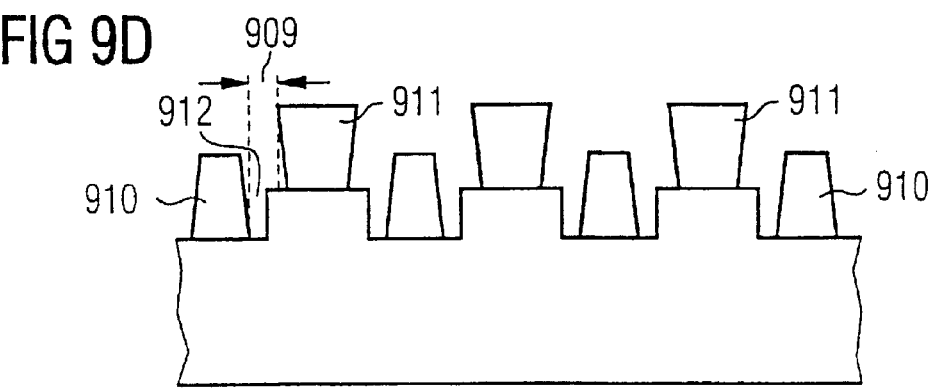

In a further step, an auxiliary layer 904 (cf. FIG. 9b) made of titanium with a thickness of approximately 10 nm is applied to the stepped insulator layer 901.

The auxiliary layer 904 may comprise tungsten and/or nickel-chromium and/or molybdenum.

It is necessary to guarantee that the metal layer applied in a further step, according to the exemplary embodiment a metal layer 907 made of gold, grows porously at the edges 905 of the steps 902 so that, in a further method step, it is possible to respectively etch a gap 908 at the step junctions into the gold layer 907 which is applied surface-wide.

The gold layer 907 for the biosensor 800 is applied in a further method step.

According to the exemplary embodiment, the gold layer has a thickness of from approximately 500 nm to approximately 2000 nm.

In terms of the thickness of the gold layer 907, it is merely necessary to guarantee that the thickness of the gold layer 907 is sufficient for the gold layer 907 to grow porously in columns.

In a further step, openings 908 are etched into the gold layer 907 so that gaps are formed.

For wet etching of the openings, an etchant solution made up of 7.5 g of Super Strip 100™ (trademark of Lea Ronal GmbH, Germany) and 20 g KCN in 1000 ml of water $H_2O$ is used.

Owing to the columnar growth of the gold, in general of the metal, during the evaporation coating onto the adhesion layer 904, anisotropic etching attack is achieved so that the surface erosion of the gold takes place approximately in the ratio 1:3.

The gaps 908 are formed as a function of the duration of the etching process by the etching of the gold layer 907.

This means that the duration of the etching process dictates the basic width, i.e. the distance 909 between the gold electrodes 910, 911 which are being formed.

After the metal electrodes have a sufficient width and the distance 909 between the gold electrodes 910, 911 which are being formed is achieved, the wet etching is ended.

It should be noted that, because of the porous evaporation coating, etching in a direction parallel to the surface of the insulator layer 901 takes place substantially faster than in a direction perpendicular to the surface of the insulator layer 901.

It should be pointed out that, alternatively to a gold layer, it is possible to use other noble metals, for example platinum, titanium or silver, since these materials can likewise have holding regions or can be coated with a suitable material for holding immobilized DNA probe molecules, or in general for holding probe molecules, and they exhibit columnar growth during evaporation coating.

For the case in which the adhesion layer 904 needs to be removed in the opened columns 912 between the metal electrodes 910, 911, this is likewise carried out in a self-aligning fashion by using the gold electrodes 910, 911 as an etching mask.

Compared with the known interdigitated electrodes, the structure according to this exemplary embodiment has the advantage, in particular, that owing to the self-aligning opening of the gold layer 907 over the edges 905, the distance between the electrodes 910, 911 is not tied to a minimum resolution of the production process, i.e. the distance 909 between the electrodes 910, 911 can be kept very narrow.

According to this method, the biosensor 800 according to the exemplary embodiment represented in FIG. 8 with the corresponding metal electrodes is therefore obtained.

Figure 10A:
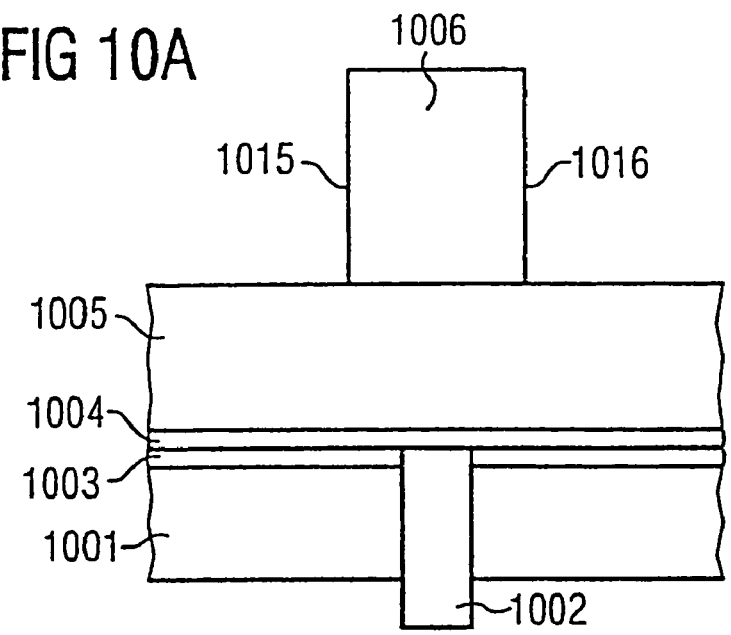
FIGS. 10a to 10c shows cross-sectional views through a biosensor during individual method steps of the method for producing an electrode of the biosensor in accordance with a further exemplary embodiment of the invention.
Figure 10B:
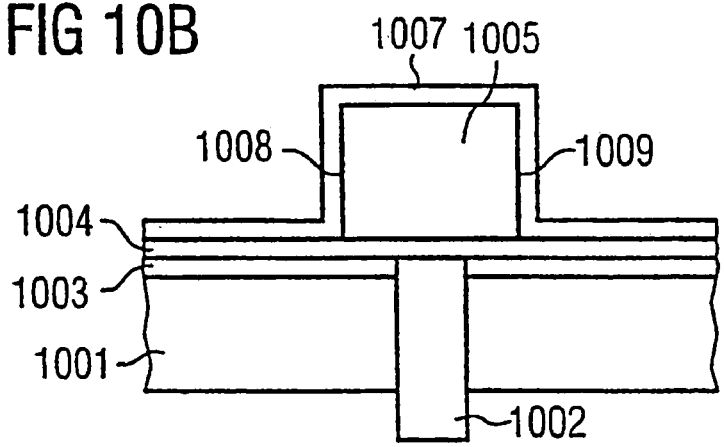
Figure 10C:
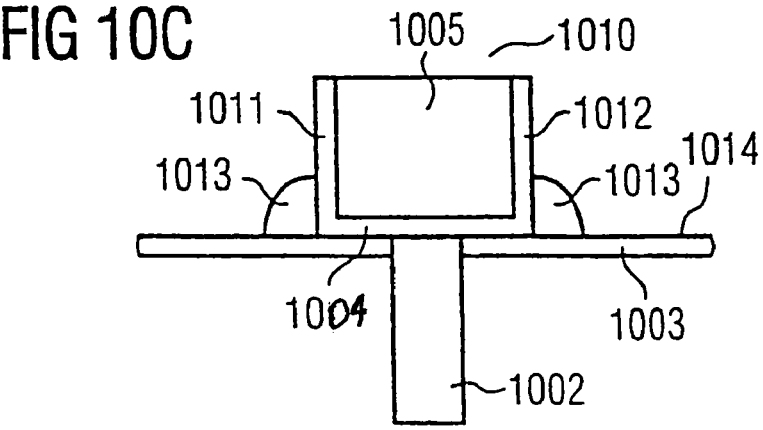

Second Method for Producing Metal Electrodes with Essentially Vertical Side Walls, Which Can Immobilize Probe Molecules The production method represented in FIG. 10*a* to FIG. 10*c* starts with a substrate 1001, for example a silicon substrate wafer (cf. FIG. 10*a*), on which metallization 1002 is already provided as an electrical terminal, an etch stop layer 1003 of silicon nitride $Si_3N_4$ already having been applied on the substrate 1001.

A metal layer 1004, according to the exemplary embodiment a gold layer 1004, is applied on the substrate by means of an evaporation coating method.

Alternatively, a sputtering method or a CVD method may also be used to apply the gold layer 1004 to the etch stop layer 1003.

In general, the metal layer 1004 comprises the metal on which the electrode to be formed is intended to be formed.

An electrically insulating auxiliary layer 1005 of silicon oxide $SiO_2$ is applied on the gold layer 1004 by means of a CVD method (alternatively by means of an evaporation coating method or a sputtering method).

By using photolithographic technology, a resist structure, for example a cuboid structure, is formed from a resist layer 1006, which corresponds to the shape of the electrode to be formed.

If a biosensor array, described below, with a plurality of electrodes is to be produced, a resist structure whose shape corresponds to the electrodes to be formed, which form the biosensor array, is produced by means of photolithography.

Put another way, this means that the lateral dimensions of the resist structure which is formed correspond to the dimensions of the sensor electrode to be produced.

After application of the resist layer 1006 and the corresponding illumination, which defines the corresponding resist structures, the resist structure is removed in the "undeveloped", i.e. unilluminated regions, for example by means of ashing or wet chemically.

The auxiliary layer 1005 is also removed by means of a wet etching method or a dry etching method in the regions not protected by the photoresist layer 1006.

In a further step, after removal of the resist layer 1006, a further metal layer 1007 is applied conformally as an electrode layer over the remaining auxiliary layer 1005, in such a way that the side faces 1008, 1009 of the residual auxiliary layer 1005 are covered with the electrode material, according to the exemplary embodiment with gold (cf. FIG. 10*b*).

The application may be carried out by means of a CVD method or a sputtering method or by using an ion metal plasma method.

In a last step (cf. FIG. 10*c*), spacer etching is carried out, during which the desired structure of the electrode 1010 is formed by deliberate over-etching of the metal layers 1004, 1007.

The electrode 1010 therefore has the spacers 1011, 1012, which have not been etched away in the etching step of etching the metal layers 1004, 1007, as well as the part of the first metal layer 1004, arranged immediately below the residual auxiliary layer 1005, which has not been etched away by means of the etching method.

The electrode 1010 is electrically coupled to the electrical terminal, i.e. the metallization 1002.

The auxiliary layer 1005 of silicon oxide may if necessary be removed by further etching, for example in the plasma or wet chemically, by means of a method in which selectivity with respect to the etch stop layer 1003 is provided.

This is guaranteed, for example, if the auxiliary layer 1005 consists of silicon oxide and the etch stop layer 1003 comprises silicon nitride.

The steepness of the walls of the electrode in the biosensor chip 700, 800, represented by the angle 1013 between the spacers 1011, 1012 and the surface 1014 of the etch stop layer 1003, is therefore determined by the steepness of the flanks of the residual auxiliary layer 1005, i.e. in particular the steepness of the resist flanks 1015, 1016 of the structured resist layer 1006.

Figure 11A:
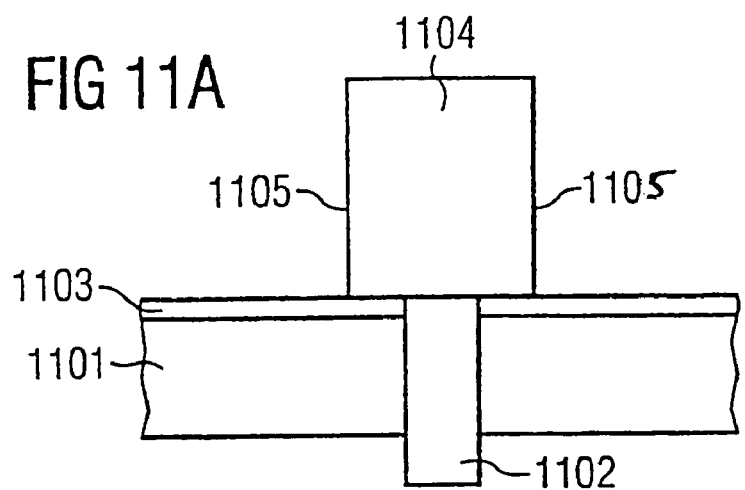
FIGS. 11a to 11c show cross-sectional views through a biosensor during individual method steps of the method for producing an electrode of the biosensor in accordance with a further exemplary embodiment of the invention.
Figure 11B:
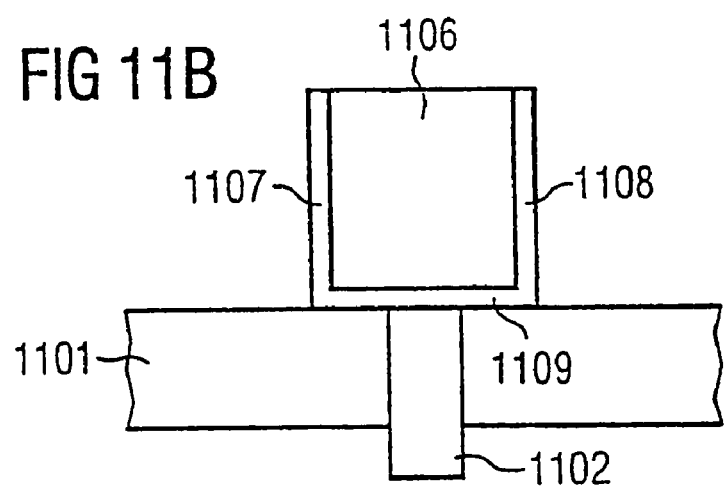
Figure 11C:
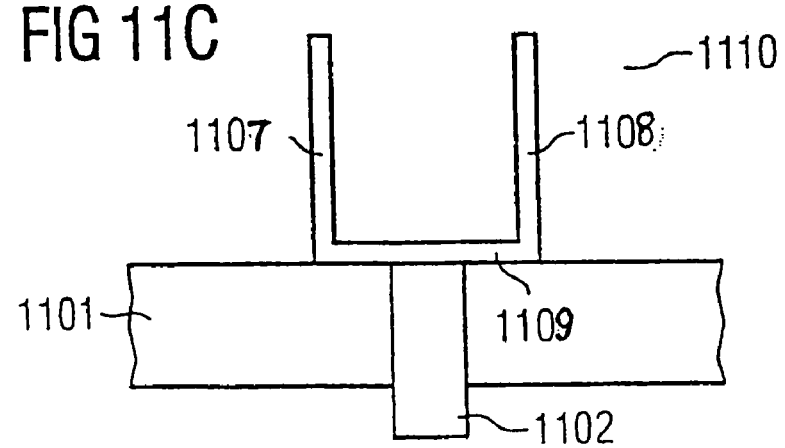

Third Method for Producing Metal Electrodes with Essentially Vertical Side Walls, Which Can Immobilize Probe Molecules FIG. 11*a* to FIG. 11*c* represent a further possibility for producing an electrode within essentially vertical walls.

This also, as represented in the second example of producing an electrode, starts with a substrate 1101 on which a metallization 1102 is already provided for the electrical terminal of the biosensor electrode to be formed.

A metal layer 1103 is evaporation coated as an electrode layer on the silicon substrate 1101, the metal layer 1103 comprising the material to be used for the electrode, according to this exemplary embodiment gold.

Alternatively to evaporation coating of the metal layer 1103, the metal layer 1103 may also be applied on the substrate 1101 by means of a sputtering method or by means of a CVD method.

A photoresist layer 1104 is applied on the metal layer 1103 and is structured by means of photolithographic technology so as to produce a resist structure which, after development and removal of the developed regions, corresponds to the lateral dimensions of the electrode to be formed, or in general of the biosensor array to be formed.

The thickness of the photoresist layer 1104 corresponds essentially to the height of the electrodes to be produced.

During structuring in a plasma with process gases which cannot lead to any reaction of the electrode material, in particular in an inert gas plasma, for example with argon as the process gas, the erosion of the material according to this exemplary embodiment is carried out by means of physical sputter erosion.

In this case, the electrode material is sputtered from the metal layer 1103 in a redeposition process onto the essentially vertical side walls 1105 of the structured resist elements that are not removed after ashing the developed resist structure, where it is no longer exposed to any sputter attack.

Redeposition of electrode material onto the resist structure protects the resist structure from further erosion.

Because of the sputtering, side layers 1107, 1108 of the electrode material, according to the exemplary embodiment of gold, are formed at the side walls 1105 of the resist structure.

The side layers 1107, 1108 are electrically coupled to an unremoved part 1109 of the metal layer 1103, which lies immediately below the residual resist structure 1106, and furthermore to the metallization 1103 (cf. FIG. 11*b*).

In a last step (cf. FIG. 11*c*), the resist structure 1106, i.e. the photoresist which is found in the volume formed by the side walls 1107, 1108 as well as the remaining metal layer 1109, is removed by means of ashing or wet chemically.

The result is the electrode structure 1110 represented in FIG. 11*c*, which is formed with the side walls 1107, 1108 as well as the unremoved part 1109, which forms the bottom of the electrode structure and is electrically coupled to the metallization 1103.

As in the production method presented above, the steepness of the side walls 1107, 1108 of the electrode that is formed in this method is determined by the steepness of the resist flanks 1105.

FIG. 12*a* to FIG. 12*c* represent a further exemplary embodiment of the invention with cylindrical electrodes protruding perpendicularly from the substrate.

In order to produce the biosensor 1200 with cylindrical electrodes, which are arranged essentially perpendicularly on a substrate 1201 of silicon oxide, a metal layer 1202 is applied by means of an evaporation coating method as an electrode layer of the desired electrode material, according to the exemplary embodiment of gold.

A photoresist layer is applied on the metal layer 1202, and the photoresist layer is illuminated by means of a mask so that the cylindrical structure 1203 represented in FIG. 12*a* is obtained on the metal layer 1202 after the unilluminated regions have been removed.

The cylindrical structure 1203 has a photoresist torus 1204 as well as a cylindrical photoresist ring 1205, which is arranged concentrically around the photoresist torus 1204.

The photoresist is removed between the photoresist torus 1204 and the photoresist ring 1205, for example by means of ashing or wet chemically.

Through the use of a sputtering method, as in conjunction with the method described above for producing an electrode, a metal layer 1206 is applied around the photoresist torus 1204 by means of a redeposition process.

In a similar way, an inner metal layer 1207 is formed around the photoresist ring 1205 (cf. FIG. 12*b*).

In a further step, the structured photoresist material is removed by means of ashing or wet chemically, so that two cylindrical electrodes 1208, 1209 are formed.

The substrate 1201 is removed in a last step, for example by means of a plasma etching process that is selective with respect to the electrode material, to the extent that the metallizations in the substrate are exposed and electrically couple to the cylindrical electrodes.

The inner cylindrical electrode 1208 is therefore electrically coupled to a first electrical terminal 1210, and the outer cylindrical electrode 1209 is electrically coupled to a second electrical terminal 1211.

The residual metal layer 1202, which has not yet been removed by the sputtering between the cylindrical electrodes 1208, 1209, is removed in a last step by means of a sputter-etching process. The metal layer 1202 is likewise removed in this way.

It should be mentioned in this context that, according to this exemplary embodiment as well, the metallizations for the electrical terminals 1210, 1211 are already provided in the substrate 1201 at the start of the method.

FIG. 13 shows a plan view of a biosensor array 1300, in which cylindrical electrodes 1301, 1302 are contained.

Each first electrode 1301 has a positive electrical potential.

Each second electrode 1302 of the biosensor array 1300 has an electrical potential that is negative in relation to the respectively neighboring first electrode 1301.

The electrodes 1301, 1302 are arranged in rows 1303 and columns 1304.

The first electrodes 1301 and the second electrodes 1302 are respectively arranged alternately in each row 1303 and each column 1304, i.e. a second electrode 1302 is respectively arranged in a row 1303 or a column 1304 immediately next to a first electrode 1301, and a first electrode 1301 is respectively arranged in a row 1303 or a column 1304 next to a second electrode 1302.

This ensures that an electric field with essentially uncurved field lines in the direction of the height of the cylinder electrodes 1301, 1302 can be produced between the individual electrodes.

As described above, a large number of DNA probe molecules are respectively immobilized on the electrodes.

If a solution to be analyzed (not shown) is then applied to the biosensor array 1300, then the DNA strands hybridize with DNA probe molecules complementary thereto which are immobilized on the electrodes.

In this way, by means of the redox recycling operation described above, the existence or nonexistence of DNA strands of a predetermined sequence in a solution to be analyzed can in turn be detected by means of the biosensor array 1300.

FIG. 14 shows a further exemplary embodiment of a biosensor array 1400 with a plurality of cuboid electrodes 1401, 1402.

The arrangement of the cuboid electrodes 1401, 1402 is in accordance with the arrangement of the cylindrical electrodes 1301, 1302 as presented in FIG. 13 and explained above.

FIG. 15 shows an electrode arrangement of a biosensor chip 1500 according to a further exemplary embodiment of the invention.

The first electrode 101 is applied on the insulator layer 103 and is electrically coupled to the first electrical terminal 104.

The second electrode 102 is likewise applied on the insulator layer 103 and is electrically coupled to the second electrical terminal 105.

As shown in FIG. 15, the second electrode according to this exemplary embodiment has a different shape compared with the second electrode described previously.

The first electrode, as can be seen from FIG. 15, is a planar electrode and the second electrode is configured with a T-shape.

Each T-shaped second electrode has a first branch 1501, which is arranged essentially perpendicular to the surface 1507 of the insulator layer 103.

Furthermore, the second electrode 102 has second branches 1502 which are arranged perpendicular to the first branch 1501 and are arranged at least partially over the surface 1503 of the respective first electrode 101.

As can be seen in FIG. 15, several first electrodes 101 and several second electrodes 102 are connected in parallel, so that because of the T-shaped structure of the second electrode 102, a cavity 1504 is created which is formed by two second electrodes 102 arranged next to one another, on first electrode 101 and the insulator layer 103.

The individual first and second electrodes 101, 102 are electrically insulated from one another by means of the insulator layer 103.

An opening 1505 is provided between the individual second branches 1502 of the second electrode 102 for each cavity 1504, which opening 1505 is large enough so that when an electrolyte 1506 is being applied to the biosensor 1500, the electrolyte and DNA strands possibly contained in the solution 1506 to be analyzed, for example an electrolyte, can pass through the opening 1505 into the cavity 1504.

DNA probe molecules 1509, which can hybridize with the corresponding DNA strands of a predetermined sequence that are to be recorded, are immobilized on holding regions on the first and second electrodes.

As can be seen in FIG. 15, because of the mutually facing surfaces, aligned essentially parallel with one another, of the second electrode 1508 and of the first electrode 1503, on which the holding regions for holding the DNA probe molecules 1509 are provided, essentially uncurved field lines are formed when an electric field is applied between the first electrode 701 101 and the second electrode 702 102.

FIG. 16 shows a biosensor 1600 according to a further exemplary embodiment of the invention.

The biosensor 1600 according to the further exemplary embodiment corresponds essentially to the biosensor 1500 explained above and shown in FIG. 15, with the difference that no holding regions with immobilized DNA probe molecules 1509 are provided on side walls of the first branch 1501 of the second electrode 102, but rather the surface 1601 of the first branch 1501 of the second electrode 102 is covered with insulator material of the insulator layer 103 or a further insulating layer.

According to the exemplary embodiment shown in FIG. 16, holding regions on the first electrode and on the second electrode 101, 102 are consequently only on directly facing surfaces of the electrodes, i.e. on the surface 1602 of the second branch of the second electrode 102 and on the surface 1603 of the first electrode 101.

FIG. 17a to FIG. 17g represent individual method steps for producing the first electrode 701 101 and the second electrode 702 102 in the biosensors 1500, 1600.

In the insulator layer 103 as a substrate, according to the exemplary embodiment made of silicon oxide, a structure whose shape corresponds to the first electrode 101 to be formed is etched into the insulator layer 103 by using a mask layer, for example made of photoresist.

Figure 17A:
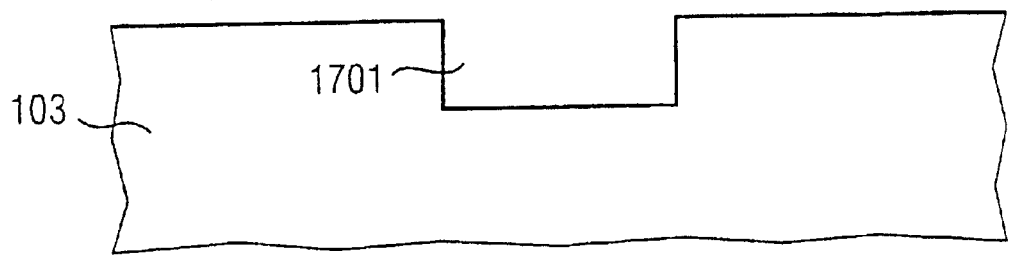
Figure 17B:
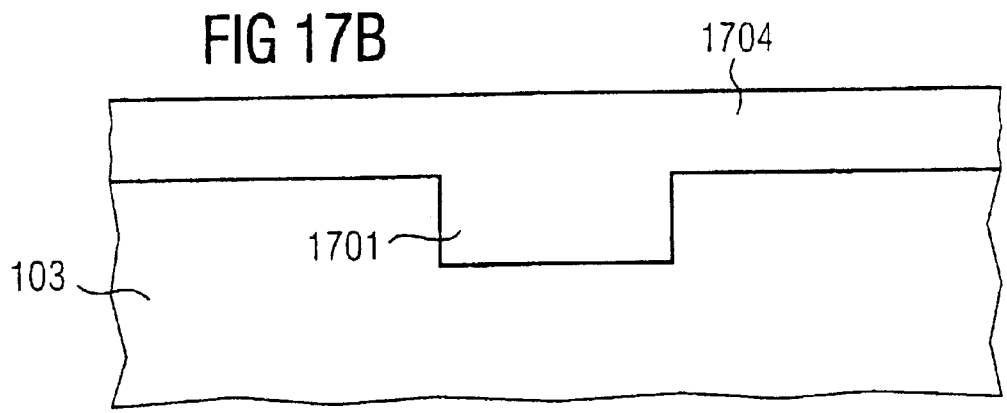

After removal of the mask layer by ashing or by a wet chemical method, a layer of the desired electrode material is applied surface-wide on the insulator layer 103, in such a way that the previously etched structure 1701 (cf. FIG. 17a) is at least completely filled; the structure 1701 may even be overfilled (cf. FIG. 17b).

Figure 17C:
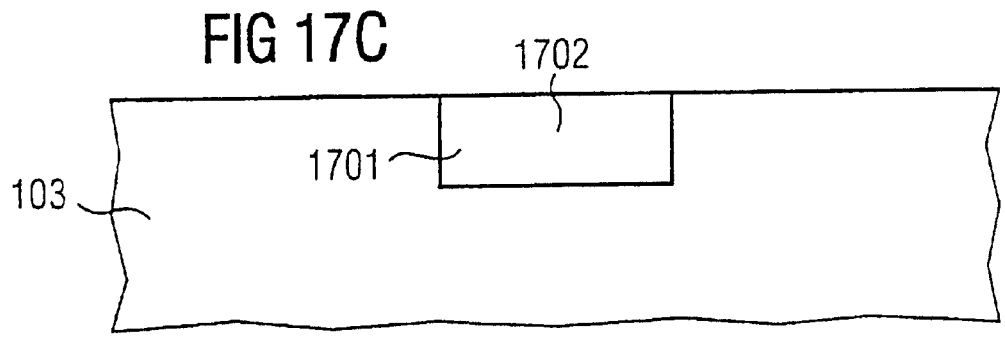

In a further step, the electrode material 1702, preferably gold, located outside the prefabricated structure 1701 is removed by means of a chemical mechanical polishing method (cf. FIG. 17c).

After the completion of the chemical-mechanical polishing method, the first electrode 101 is therefore embedded flush in the insulator layer 103.

Electrode material 1702 outside, i.e. between the further second electrodes 102 or between the first electrodes 101, is removed without leaving any residue.

Figure 17D:
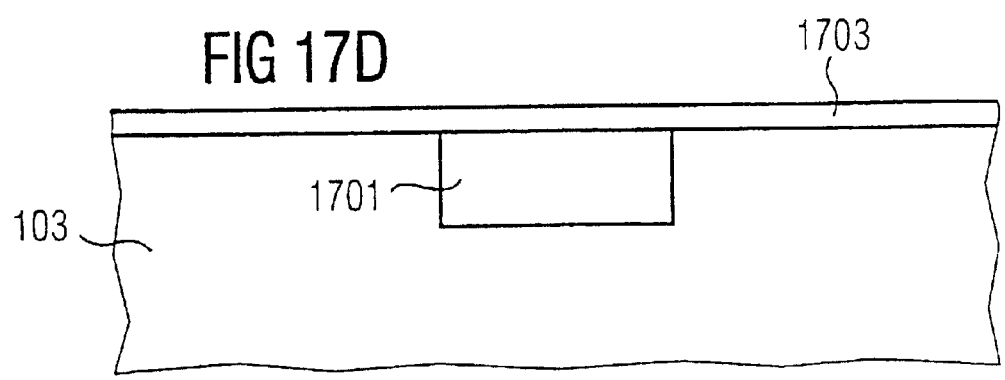

A cover layer 1703, for example made of silicon nitride, may furthermore be applied to the first electrode 101 by means of a suitable coating method, for example a CVD method, a sputtering method or an evaporation coating method (cf. FIG. 17d).

FIG. 17e shows several first electrodes 1701 made of gold, which are embedded next to one another in the insulator layer 103, and the cover layer 1703, located on top.

In a further step (cf. FIG. 17f), a second electrode layer 1704 is applied on the cover layer 1703.

After masking has been completed, taking account of the desired opening between the second electrodes, which is to be formed from the second electrode layer 1704, the desired openings 1705 are formed, and the second electrode layer 1704 is etched by means of a dry etching process in a downstream plasma, in such a manner that the desired cavity 1504 is formed in accordance with the biosensors 1500, 1600 illustrated in FIG. 15 or FIG. 16 (cf. FIG. 17g).

It should be noted in this context that the cover layer 1703 is not absolutely necessary, but it is advantageous in order to protect the first electrodes 101 from superficial etching during the formation of the cavity 1504.

In an alternative embodiment, the T-shaped structure of the second electrode 102 may be formed as follows: after forming the first electrode 101 according to the method described above, a further insulator layer is formed by means of a CVD method or another suitable coating method on the first insulator layer or, if the cover layer 1703 exists, on the cover layer 1703. Subsequently, corresponding trenches are formed in the cover layer 1703, which are used to accommodate the first branch 1501 of the T-shaped structure of the second electrode 102. These trenches are filled with the electrode material gold and, according to the damascene method, the electrode material is removed which has been formed in the trenches and above the second insulator layer by means of chemical-mechanical polishing, down to a predetermined height which corresponds to the height of the second branch 1502 of the T-shaped second electrode 102.

The opening 1505 between the second electrodes 102 is formed by means of photolithography, and the insulator material is subsequently removed, and at least partially, by means of a dry etching method in a downstream plasma from the volume which is intended to be formed as the cavity 1504.

It should furthermore be pointed out that the embodiments described above are not restricted to an electrode whose holding region is produced by means of gold. Alternatively, electrodes may be coated with materials in the holding regions, for example with silicon monoxide or silicon dioxide, which can form a covalent bond with the amine, acetoxy, isocyanate, alkylsilane radicals referred to above, in order to immobilize probe molecules, in this variant in particular in order to immobilize ligands.

FIG. 18 shows a further electrode arrangement 1800 having a plurality:
of circular first electrodes 1801, on each of which there is a holding region for immobilizing probe molecules,
of circular second electrodes 1802,
of circular third electrodes 1803.

The electrodes are arranged alternately and concentrically around one another, in such a manner that in each case a third electrode is arranged between the first electrode and the second electrode.

The electrodes may be designed both as planar electrodes and as cylindrical electrodes with substantially vertical side walls which are produced using the method described above.

FIG. 19 shows a plan view of a biosensor array 1900 in accordance with a further exemplary embodiment of the invention with cylindrical electrodes 1901, 1902, 1903, in which the electrodes together with their associated electrical potentials are illustrated.

The first electrical potential V1 is applied to each first electrode 1901. The second electrical potential V2 is applied to each second electrode 1902. The third electrical potential V3 is applied to each third electrode 1903, in the same way as has been explained in connection with the exemplary embodiments described above.

As an alternative or in addition, the biosensor array 1900 may also have cuboidal electrodes.

The following publications have been cited in this document:

[1] R. Hintsche et al., Microbiosensors Using Electrodes Made in Si-Technology, Frontiers in Biosensorics, Fundamental Aspects, edited by F. W. Scheller et al., Dirk Hauser Verlag, Basle, pp. 267–283, 1997

[2] N. L. Thompson, B. C. Lagerholm, Total Internal Reflection Fluoresence: Applications in Cellular Biophysics, Current Opinion in Biotechnology, Vol. 8, pp. 58–64, 1997

[3] P. Cuatrecasas, Affinity Chromatography of Macromolecules, Advances in Enzymology, Vol. 36, pp. 29–89, 1972

[4] P. van Gerwan, Nanoscaled Interdigitated Electrode Arrays for Biochemical Sensors, IEEE, International Conference on Solid-State Sensors and Actuators, Chicago, pp. 907–910, 16–19 Jun. 1997

[5] M. Paeschke et al, Voltammetric Multichannel Measurements Using Silicon Fabricated Microelectrode Arrays, Electroanalysis, Vol. 7, No. 1, pp. 1–8, 1996

[6] R. Hintsche et al, Microbiosensors using electrodes made in Si-technology, Frontiers in Biosensorics, Fundamental Aspects, edited by F. W. Scheller et al, Birkhauser Verlag, Basle, Switzerland, 1997.

The invention claimed is:

1. A biosensor, comprising:
a first electrode having a first electrical potential, wherein the first electrode has a holding region for holding probe molecules which can bind macromolecular biopolymers;
a second electrode having a second electrical potential;
a third electrode having a third electrical potential, wherein the second electrode and the third electrode are designed in such a manner that a reduction/oxidation process takes place as part of a reduction/oxidation recycling operation at the second electrode and at the third electrode; and
the third electrical potential being selected in such a manner that during reduction/oxidation recycling operation, the reduction or oxidation takes place only at the second electrode and at the third electrode thereby shielding the first electrode from cleaved part-molecules of the reduction/oxidation recycling operation.

2. The biosensor as claimed in claim 1,
in which the third electrical potential is greater than the first electrical potential, and
in which the first electrical potential is greater than the second electrical potential.

3. The biosensor as claimed in claim 1 in which the holding region of the first electrode is coated with a material which can immobilize probe molecules.

4. The biosensor as claimed in claim 1 in which the holding region of the first electrode is designed to hold ligands to which peptides or proteins can be bound.

5. The biosensor as claimed in claim 1 in which the holding region of the first electrode is designed to hold DNA probe molecules to which DNA molecules can be bound.

6. The biosensor as claimed in claim 1, further comprising at least two first electrodes, each first electrode having an electrical potential and a holding region for holding probe molecules which can bind macromolecular biopolymers; wherein the each of the holding regions of the at least two first electrodes include at least one of the materials selected from the group consisting of hydroxyl radicals, epoxy radicals, amine radicals, acetoxy radicals, isocyanate radicals, succinimidyl ester radicals, thiol radicals, gold, silver, platinum, and titanium.

7. The biosensor as claimed in claim 1 in which the electrodes are arranged in an interdigitated electrode arrangement, the third electrode in each case being arranged between the first electrode and the second electrode.

8. The biosensor as claimed in claim 1 in which the electrodes are arranged in circular form concentrically around one another, the third electrode in each case being arranged between the first electrode and the second electrode.

9. The biosensor as claimed in claim 1 in which the first electrode and the second electrode and/or the third electrode are arranged in such a manner relative to one another that substantially uncurved field lines of an electric field which is generated between the first electrode and the second electrode and/or the third electrode can form between the first electrode and the second electrode and/or the third electrode.

10. A biosensor array, comprising:
a multiplicity of first electrodes having a first electrical potential, wherein the multiplicity of first electrodes have a holding region for holding probe molecules which can bind macromolecular biopolymers;
a multiplicity of second electrodes having a second electrical potential;

a multiplicity of third electrodes having a third electrical potential, the second electrodes and the third electrodes being designed in such a manner that a reduction/oxidation process takes place as part of a reduction/oxidation recycling operation at the second electrodes and at the third electrodes; and the third electrical potential being selected in such a manner that during reduction/oxidation recycling operation, the reduction or oxidation takes place only at the second electrode and at the third electrode thereby shielding the first electrode from cleaved part-molecules of the reduction/oxidation recycling operation.

11. A method for detecting macromolecular biopolymers using a biosensor which has:

a first electrode, having a first electrical potential, wherein the first electrode has a holding region for holding probe molecules which can bind macromolecular biopolymers, a second electrode having a second electrical potential;

a third electrode having a third electrical potential, wherein the second electrode and the third electrode are designed in such a manner that a reduction/oxidation process takes place as part of a reduction/oxidation recycling operation at the second electrode and at the third electrode;

the third electrical potential being selected in such a manner that during reduction/oxidation recycling operation, the reduction or oxidation takes place only at the second electrode and at the third electrode thereby shielding the first electrode from cleaved part-molecules of the reduction/oxidation recycling operation, the method comprising:

bringing a solution which is to be analyzed into contact with the biosensor, it being possible for the solution to contain the macromolecular biopolymers which are to be recorded;

binding macromolecular biopolymers which are present in the solution which is to be analyzed to probe molecules on the first electrodes, the bound macromolecular biopolymers being marked with an enzyme;

rinsing the biosensor with a rinsing solution, so that the solution which is to be analyzed is removed;

bringing a further solution containing molecules which can be cleaved by the enzyme into contact with the biosensor;

cleaving in each case one cleavable molecule into a first part-molecule having a first charge and a second part-molecule having a second charge;

oxidizing or reducing the first part-molecule at the third electrode, the oxidized or reduced first part-molecule being reduced or oxidized at the second electrode, so that a reduction/oxidation recycling operation is carried out between the third electrode and the second electrode thereby shielding the first electrode from said cleaved part-molecules; and determining the macromolecular biopolymers as a function of the reduction/oxidation recycling operation.

12. The method as claimed in claim 11, in which the enzyme used is an enzyme selected from the group consisting of the following classes NADH-independent dehydrogenase, and phenoloxidase.

13. The method as claimed in claim 11 in which a first electrical potential is applied to the first electrode, the method comprising:

applying a second electrical potential to the second electrode;

applying a third electrical potential to the third electrode; and selecting electrical potential in such a manner that during the reduction/oxidation recycling process, the reduction or oxidation takes place only at the second electrode and at the third electrode.

14. The method as claimed in claim 13, further comprising:

selecting the third electrical potential to be greater than the first electrical potential; and selecting the first electrical potential to be greater than the second electrical potential.

* * * * *